US012207927B2

(12) United States Patent
Bouchon et al.

(10) Patent No.: US 12,207,927 B2
(45) Date of Patent: Jan. 28, 2025

(54) SYSTEMS AND METHODS FOR EVALUATING AND IMPROVING NEUROTRANSMITTER LEVELS BASED ON MOBILE DEVICE APPLICATION DATA

(71) Applicant: Matter Neuroscience Inc., Boulder, CO (US)

(72) Inventors: Axel Bouchon, Kleinmachnow (DE); Ben Goldhirsh, Beverly Hills, CA (US)

(73) Assignee: Matter Neuroscience Inc., Boulder, CO (US)

(*) Notice: Subject to any disclaimer, the term of this patent is extended or adjusted under 35 U.S.C. 154(b) by 607 days.

(21) Appl. No.: 17/389,023

(22) Filed: Jul. 29, 2021

(65) Prior Publication Data

US 2022/0031212 A1  Feb. 3, 2022

Related U.S. Application Data

(60) Provisional application No. 63/059,738, filed on Jul. 31, 2020.

(51) Int. Cl.
  *A61B 5/16* (2006.01)
  *A61B 5/00* (2006.01)

(52) U.S. Cl.
  CPC ............... *A61B 5/165* (2013.01); *A61B 5/72* (2013.01); *A61B 5/7475* (2013.01)

(58) Field of Classification Search
  CPC ......... A61B 5/165; A61B 5/72; A61B 5/7475; G16H 20/70; G16H 20/10; G16H 50/20; G16H 50/30
  See application file for complete search history.

(56) References Cited

U.S. PATENT DOCUMENTS 10,091,554 B1* 10/2018 Newell ............... H04N 21/4532
2012/0045740 A1* 2/2012 Zak ......................... G09B 19/00
434/236

(Continued)

FOREIGN PATENT DOCUMENTS

CN        107967329 A     4/2018

OTHER PUBLICATIONS

Wikipedia, Matrix (mathematics), https://en.wikipedia.org/wiki/Matrix_(mathematics) (Year: 2024).*

(Continued)

*Primary Examiner* — Jonathan T Kuo
(74) *Attorney, Agent, or Firm* — Morrison & Foerster LLP

(57) ABSTRACT

Systems and methods for evaluating and improving overall mental health of an individual are presented herein. In one or more examples, the systems and methods can be implemented in a computer application that is configured to download information from a user's mobile device. Once the data is acquired, in one or more examples, the application can prompt the user to provide additional information, and using both the user's input and the acquired data, the application can calculate a metric known as "Return on Happiness" (ROH) which can provide the user with a quantative measure of their happiness. In one or more examples, the ROH metric can be based on neurotransmitter activity in the user that is estimated by the application. The application can further identify any deficiencies in ROH and suggest one or more activities that the user can engage in to mitigate any of the detected deficiencies.

48 Claims, 27 Drawing Sheets

(56) References Cited

U.S. PATENT DOCUMENTS

| | | | |
|---|---|---|---|
| 2016/0270717 A1* | 9/2016 | Luna ...................... | A61B 5/743 |
| 2017/0200388 A1* | 7/2017 | Otsuka ................... | G09B 19/22 |
| 2018/0256078 A1* | 9/2018 | Vaterlaus ............. | A61B 5/7435 |
| 2018/0336575 A1* | 11/2018 | Hwang .............. | G06Q 30/0201 |
| 2019/0361872 A1* | 11/2019 | Wulf ................... | H04M 3/5175 |
| 2020/0265941 A1* | 8/2020 | Moskowitz ............ | G16H 20/70 |

OTHER PUBLICATIONS

International Search Report and Written Opinion mailed Oct. 22, 2021, directed to International Application No. PCT/US2021/043760; 16 pages.

\* cited by examiner

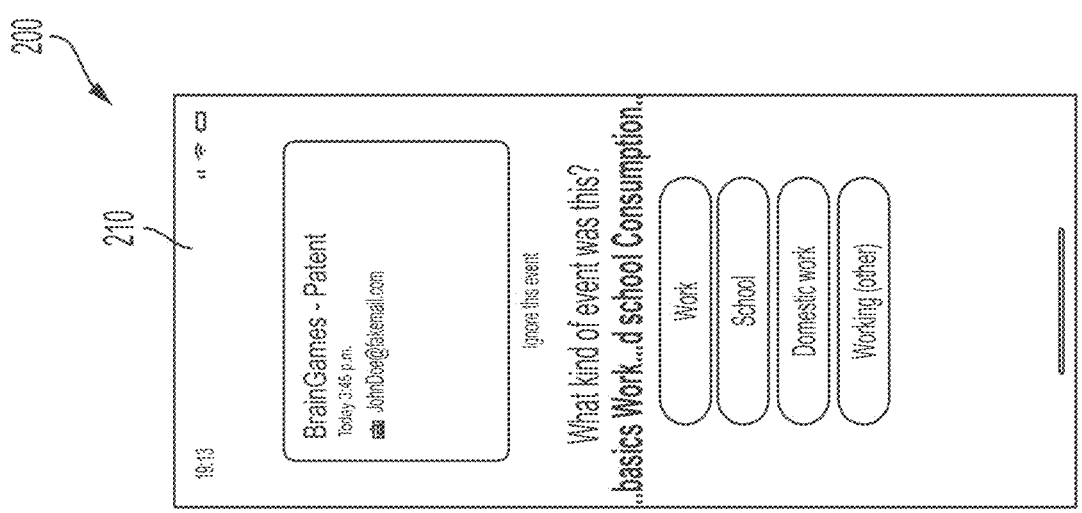
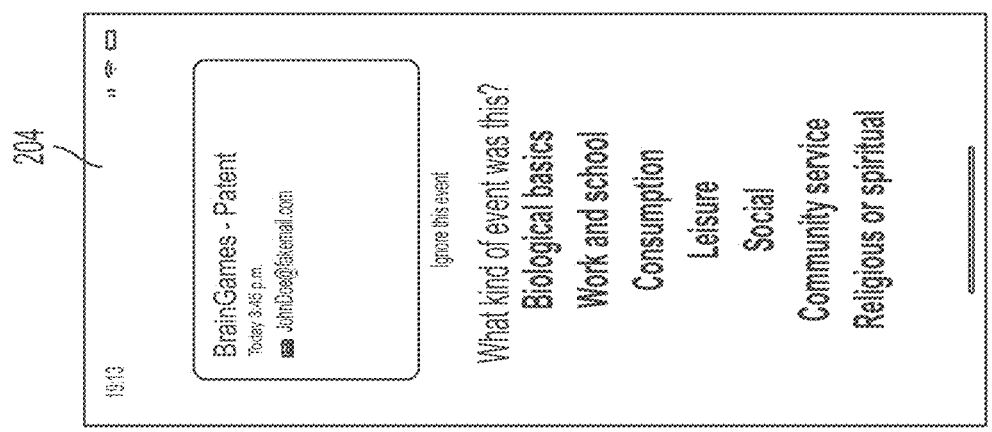
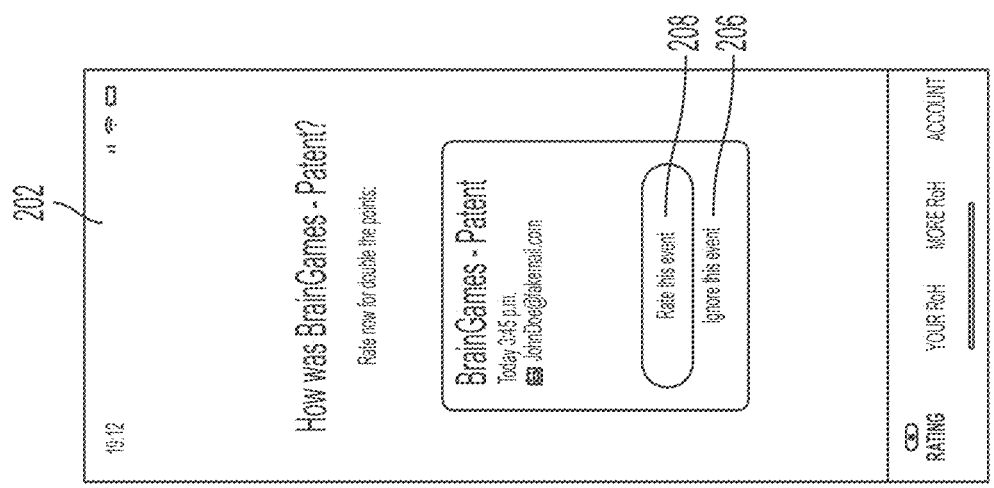
FIG. 2

B - PE - Matrix

300

Positive Emotions (PE)

| Behaviors (B) | EN | SD | PR | NL | CO | AM | AL | PL | GR |
|---|---|---|---|---|---|---|---|---|---|
| Biological Basics | | | | | | | | | |
|   Sleeping | 1 | 0 | 0 | 0 | 0 | 0 | 0 | 0 | 0 |
|   Eating/drinking | 1 | 0 | 0 | 0 | 0 | 0 | 0 | 0 | 0 |
|   Having sex | 1 | 1 | 0 | 0 | 0 | 0 | 1 | 1 | 0 |
| Work & school | | | | | | | | | |
|   Work | 1 | 0 | 1 | 0 | 1 | 0 | 1 | 1 | 1 |
|   School | 1 | 0 | 1 | 0 | 1 | 0 | 1 | 1 | 1 |
|   Domestic Work | 1 | 0 | 1 | 1 | 1 | 0 | 0 | 1 | 1 |
|   Work (other) | 1 | 0 | 1 | 0 | 1 | 0 | 1 | 1 | 1 |
| Consumption | | | | | | | | | |
|   Shopping (in person) | 1 | 0 | 1 | 0 | 0 | 1 | 0 | 1 | 0 |
|   In-person Services | 1 | 0 | 1 | 0 | 0 | 1 | 0 | 1 | 0 |
|   Online Shopping | 1 | 0 | 1 | 0 | 0 | 1 | 0 | 1 | 0 |
|   Shopping (other) | 1 | 1 | 1 | 0 | 0 | 1 | 1 | 1 | 0 |
| Leisure | | | | | | | | | |
|   Reading | 1 | 0 | 0 | 0 | 1 | 1 | 0 | 1 | 1 |
|   Reading (online) | 1 | 0 | 0 | 0 | 1 | 1 | 0 | 1 | 1 |
|   Doing sports | 1 | 0 | 1 | 0 | 1 | 1 | 1 | 1 | 1 |
|   Playing music/theatre | 1 | 0 | 1 | 0 | 1 | 1 | 1 | 1 | 1 |
|   Photography | 1 | 0 | 1 | 0 | 1 | 1 | 1 | 1 | 1 |
|   Videography | 1 | 0 | 1 | 0 | 1 | 1 | 1 | 1 | 1 |
|   Watching Entertainment | 1 | 1 | 0 | 0 | 1 | 1 | 0 | 1 | 0 |
|   Listening to music | 1 | 0 | 0 | 0 | 1 | 1 | 0 | 1 | 0 |
|   Playing video games | 1 | 0 | 1 | 0 | 0 | 1 | 1 | 1 | 0 |
|   Social Media | 1 | 1 | 1 | 1 | 0 | 1 | 1 | 1 | 0 |
|   Painting | 1 | 0 | 1 | 0 | 1 | 0 | 1 | 1 | 1 |
|   Meditation | 1 | 0 | 1 | 0 | 1 | 0 | 1 | 1 | 1 |
|   Leisure (other) | 1 | 1 | 1 | 0 | 0 | 1 | 1 | 1 | 0 |
| Social | | | | | | | | | |
|   Activities with family | 1 | 0 | 1 | 1 | 1 | 1 | 0 | 1 | 1 |
|   Activities with friends | 1 | 0 | 1 | 0 | 1 | 1 | 1 | 1 | 1 |
|   Social (other) | 1 | 1 | 1 | 0 | 1 | 1 | 0 | 1 | 1 |
| Community service | | | | | | | | | |
|   Teaching (school university) | 1 | 0 | 1 | 0 | 1 | 0 | 1 | 1 | 1 |
|   Coaching | 1 | 0 | 1 | 0 | 1 | 0 | 1 | 1 | 1 |
|   Teaching (other) | 1 | 0 | 1 | 0 | 1 | 0 | 1 | 1 | 1 |
|   Child care | 1 | 0 | 1 | 0 | 1 | 0 | 1 | 1 | 1 |
|   Elderly care | 1 | 0 | 1 | 0 | 1 | 0 | 1 | 1 | 1 |
|   Police & Fire Department | 1 | 0 | 1 | 0 | 1 | 0 | 1 | 0 | 1 |
|   Rescue & Healthcare | 1 | 0 | 1 | 0 | 1 | 0 | 1 | 0 | 1 |
|   Military | 1 | 0 | 1 | 0 | 1 | 0 | 1 | 0 | 1 |
|   Community service (other) | 1 | 0 | 1 | 0 | 1 | 0 | 1 | 0 | 1 |
| Religious or Spiritual | 1 | 0 | 1 | 0 | 1 | 0 | 1 | 0 | 1 |

FIG. 3

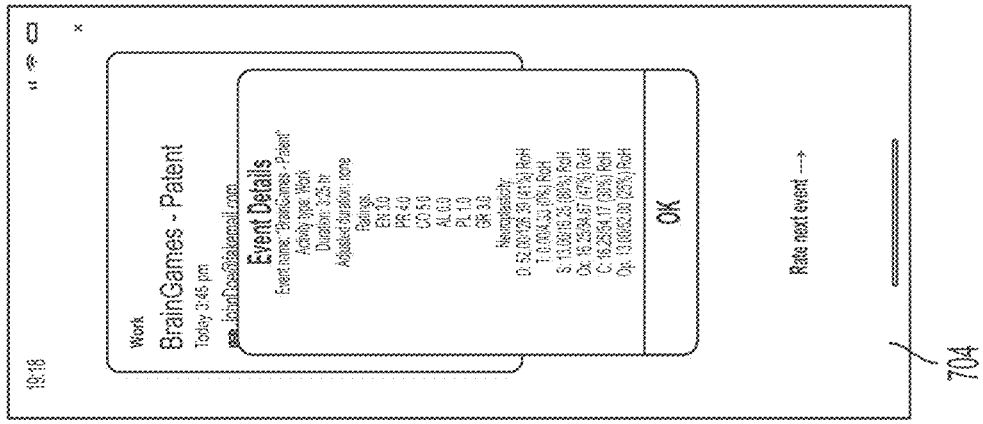
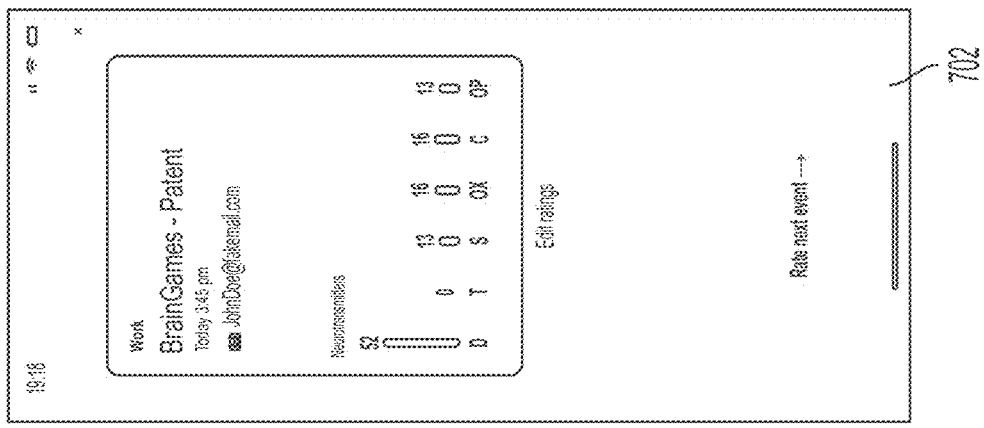
FIG. 7

| Real-world RoHmax Values - all adjustments | Day | Week 7 | Months 30 | Quarter 120 | Year 365 | |
|---|---|---|---|---|---|---|
| Real-world maximum Dopamine | 700 | 4,900 | 21,000 | 84,000 | 255,500 | Maximum RoH and neurotransmitter values used as a reference in the RoH app |
| Real-world maximum Testosterone | 24 | 168 | 720 | 2,880 | 8,760 | |
| Real-world maximum Serotonin | 90 | 630 | 2,700 | 10,800 | 32,850 | |
| Real-world maximum Oxytocin | 192 | 1,344 | 5,760 | 23,040 | 70,080 | |
| Real-world maximum Cannabinoids | 300 | 2,100 | 9,000 | 36,000 | 109,500 | |
| Real-world maximum Opioids | 288 | 2,016 | 8,640 | 34,560 | 105,120 | |
| Real-world RoHmax | 1,594 | 11,158 | 47,820 | 191,280 | 581,810 | |

FIG. 8B (Continued)

1104 — Testosterone

| | Overstimulation | Understimulation | Optimum |
|---|---|---|---|
| | Reflect upon, only sporadically consume or try to avoid behaviors that are designed to be addictive (e.g. Instagram, Youtube, video gaming) | It might be simply missed - we rarely journal activities linked to sexual desire. Put it in from now on (encrypt it!). | It might be simply missed - we rarely journal activities linked to sexual desire. Put it in from now on (encrypt it!). |
| | Reflect upon, only sporadically use or try to avoid taking stimulating drugs | Avoid routine | Sexual desires are fundamentally blocked by social and educational norms. Allow yourself to think and reflect outside the norms |
| | Reflect upon, only sporadically use stimulating food (e.g. high fat, sugar), beverages (e.g. sugar, caffeine) | If you are in a partnership, reflect why you do not experince sexual desire. | Be honest to yourself what is sexually attracting you (don't care what others say) |
| FROM FIG. 11A | Reflect upon, only sporadically use stimulating nutritional supplements (e.g. Phenylalanine, Tyrosine) | If you are in a partnership but too stressed, reserve a dedicated date for the two of you | Design scenes or reflect situations in your mind that trigger your sexual desire. Talk about it to your partner, if it feels appropriate | TO FIG. 11C |
| | Sleep enough (6-8 hours). Sleep is active happiness management. Increasing Your RoH by cutting on sleep only works short-term but it is devasting long-term | If you are in a partnership with your kids, organize a nanny while you meet your partner in a hotel nearby | Get experimental. Whatever you do, always think about the other side, never hurt someone (emotionally, physically) |
| | Dopamine is the critical cofactor for all positive emotions. That means any positive emotions releases Dopamine. | You don't need a partner to enjoy sexual desire. Try to trigger your sexual desire by yourself if you miss it | Enhance Testosterone by pushing dopamine: Embrace uncertainty- allow to be surprised. Be spontanous. |
| | | Always check: What do you miss? Do not compensate missing love/partnership with sexual desire | Always check: What do you miss? Do not compensate missing love/partnership with sexual desire |
| | | Hormone level and certain medications critically influence sexual desire. Check with your physician. | |
| | | Hormone level and certain medications critically influence sexual desire. Check with your physician. | |

FIG. 11B

| Peak | Overstimulation |
|---|---|
| Enhance beyond Testosterone: passion, risk, surprise (Dopamine), positive recognition to each other (Serotonin), touch (Oxytocin), laugh & embrace orgasm (opioids) | Reflect upon and potentially reduce the time spend with pornography. It negatively influences your hurdle to enjoy sexual desire naturally/normally. |
| Talk about your wishes. And just live them in reality. | Reflect upon and potentially adjust your time on dating apps (e.g. Grindr, Tinder). It negatively influences your hurdle to enjoy sexual desire naturally/normally. |
| Eternal memories: design and do activities you never would like to forget. Always add uncertainty | Reflect upon and potentially adjust the amount of drugs you use to enhance sexual desire. It destroys your ability to enjoy natural sexual desire. |
| | Always check: What do you miss? Do not mix up missing sexual desire and missing love/partnership. |

FROM FIG. 11B

FIG. 11C

1204 → Oxytocin

| | Overstimulation | Understimulation | Optimum |
|---|---|---|---|
| | Reflect upon and potentially adjust the amount of drugs you use to push Serotonin, e.g. Ecstasy, MDMA. It destroys your ability to enjoy real pride and recognition. | Increase all activities with positive physical interaction, e.g. hugging, touching, kissing - important: only works if both/all parties have a positive experience | Increase all activities with positive physical interaction, e.g. hugging, touching, kissing - important: only works if both/all parties have a positive experience |
| | Check? Pathologically exceeded pride can be experienced as hubris, a foolish pride or dangerous overconfidence often in combination with arrogance. | Eating together. Feeding each-other is a strong booster for Oxytocin release rarely practiced anymore | Eating together. Feeding each-other is a strong booster for Oxytocin release rarely practiced anymore |
| FROM FIG. 12A | Check: What do you miss? Don't use success in business or monetary wealth as a fake surrogate for social recognition | If you do not have a family or kids, do not worry. Contentment is a great and very effective source for Oxytocin as well | Any positive activity with your direct family, spouse, kids, mother, father, sister, brother, grandmother, grandfather | TO FIG. 12C |
| | Don't increase your self-esteem at the expense of others - it triggers Dopamine not Serotonin. Never bully individuals with fragile self-esteem, it triggers depression! | | Any care giving or teaching activity for young or helpless individuals such as children, handicapped or elderly people |
| | Be honest to yourself how many people really admire you because of the good person you are and not the money or power you have. | | Throughout your life build contentment as the second very effective source of Oxytocin. It will become in particular important when you age or the kids move out |
| | | | |
| | | | |
| | | | |

FIG. 12B

| Peak | Overstimulation |
|---|---|
| Increase all activities with positive physical interaction, e.g. hugging, touching, kissing - important: only works if both/all parties have a positive experience | Helicopter mother, momanager: stop overprotecting your kids for the sake of managing your fear to lose them. You are not responsible for their happiness. They are. |
| If you are a woman: Giving birth is the peak-of-the-peaks | Helicopter father: stop overprotecting your kids for the sake of managing your fear to lose them. You are not responsible for their happiness. They are. |
| If you are a man: hugging your baby or kids is the peak-of-the-peaks | Hyper-jealous farther and partner: be aware, Oxytocin drives jealousy and aggressive defense of the family in men. Reflect it, control it and then stop acting like a fool. |
| Eternal memories: design and do activities with your kids and family you never would like to forget. Carefully add uncertainty - keeping them safe is critical | Caring for the family can lead to Oxytocin desensitization driving guilt and depression. Please take a break: Oxytocin only works if all parties have a positive experience |
| Build and enjoy contentment - it is primarily a result of reflection and the decision to live peaceful, release everything that makes us feel anxious and dissatisfied | |
| | |
| | |
| | |

FROM FIG. 12B

Cannabinoids — 1302

| Understimulation | Optimum | Peak | Overstimulation |
|---|---|---|---|
| A lot of activities can boost cannabinoids. You can get them from friendship, contentment or amusement | A lot of activities can boost cannabinoids. You can get them from friendship, contentment or amusement | Eternal memories: design and do activities with your friends you never would like to forget. Add a lot of uncertainty, add fun, add some risk, but don't hurt anyone. | Reflect upon and reduce cannabis consumption to a minimum. It suppresses tears instead of addressing them, induces memory loss, suppresses your greatness |
| If you miss friends, amuse yourself | All activities with true friends and - to a lesser extent - with people you are positive about | Given the emotional intensity necessary to maintain and enjoy a true friendship, be aware that high ratings in cannabinoids come from very few best friends | The more friends you claim to have (e.g. social media "friends") the lesser will be your cannabinoid release. Instead you release Serotonin (recognition) |
| | Play. Go out, play your best friends! | Build real friendships: mutual commitment to each other's happiness; reciprocal liking intimacy, shared activity, common values & mutual respect | Be aware that digital friends (social media) can trigger Cannabinoid release. You have to know them in real-life# |
| | All activities that make you laugh - Laugh as much as you can | Build and enjoy contentment - it is primarily a result of reflection and the decision to live peaceful, release everything that makes us feel anxious and dissatisfied | Don't laugh at the expense of others, it is not releasing cannabinoids. It is not amusement but short-term; negative pride = zero neuroplasticity. |
| | Entertain yourself optimally with others joining | Just watch, listen to and learn from kids having fun playing with each other, laughing. Kids are ultimate leaders in releasing cannabinoids | |

Opioids — 1304

| Understimulation | Optimum | Peak | Overstimulation |
|---|---|---|---|
| Reflect what are activities that you like, you enjoy. Try to increase the amount of these activities over time. | All activities that you enjoy or like - with euphoria being the extreme. Use any positive person or friend as an amplifier. | Reach euphoria and ecstasy in your life. Without opioid-stimulating drugs. | Don't do drugs or behaviors overstimulating pleasure. They increasing your hurdle rate to experience pleasure to levels that can't be achieved naturally. |
| If you do not experience any pleasure over a longer period of time and you can't change it by yourself, please see your therapist or physician | Leave a certain level of surprise and uncertainty to your activities because 'unexpected pleasure' drives much more neuroplasticity than 'planned pleasure'. | Eternal memories: design and do activities with your family or friends you never would like to forget. Add a grain of uncertainty, make it an adventure, add fun. | Check, reflect, potentially adjust: Do you enjoy the pleasure during the activity per se (OK) or do you only crave for the pleasure feeling at the end (emerging addiction)? |
|  | Orgasmic pleasure is the best built-in drug we have in our body. So, have an orgasm once in a while. | Orgasmic pleasure is the best built-in drug we have in our body. So, let's have more orgasms and more intensive ones. Works best with joint orgasms by the way. |  |
|  | Start understanding gratitude - it is first of all a mindset only then it can turn into activities. Reflect your life once a day and be grateful on what you have got & achieved. | Provide unexpected pleasure to others understanding how much it will give to them |  |
|  | Show appreciation and return kindness | Fully embrace gratitude, as the highest positive emotion: appreciation, affirmation of goodness, understanding that gratitude is gratis & outside ourselves |  |

FROM FIG. 13A

FIG. 13B

| | 1 | 2 | 3 | 4 | 5 | 6 | 7 | 8 | 9 |
|---|---|---|---|---|---|---|---|---|---|
| | | | | Retention vs Rating started | | Retention vs ROH installed | | Retention vs Randomized | |
| | | | Number of participants | Daily ROH recording | >2 in-app activities/day | Daily ROH recording | >2 in-app activities/day | Daily ROH recording | >2 in-app activities/day |
| A | Contacted | 100 | | | | | | | |
| B | Interested in trial | 84 | | | | | | | |
| C | Selected & randomized | 50 | | | | | | | |
| D | ROH onboarding session | 50 | | | | | | | |
| E | ROH app received | 50 | | | | | | | |
| F | ROH app installed | 43 | | | | | | | |
| G | Rating started | 33 | ROH test - START | | | | | | |
| H | Continuous rating at 28 days | 17 | ROH test - STOP | 52% | 38% | 40% | 29% | 34% | 25% |
| I | Continuous rating at 42 days | 11 | 1. Follow-up period | 33% | 29% | 26% | 22% | 22% | 19% |
| J | Continuous rating at 56 days | 8 | 2. Follow-up period | 24% | 16% | 19% | 12% | 16% | 11% |
| K | Continuous rating at 90 days | 8 | 3. Follow-up period | 24% | not measured | 19% | not measured | 16% | not measured |

FIG. 17

SYSTEMS AND METHODS FOR EVALUATING AND IMPROVING NEUROTRANSMITTER LEVELS BASED ON MOBILE DEVICE APPLICATION DATA

CROSS-REFERENCE TO RELATED APPLICATION

This application claims the priority of U.S. Provisional Application No. 63/059,738, filed Jul. 31, 2020, the entire contents of which is incorporated herein by reference.

FIELD OF THE DISCLOSURE

This disclosure relates to systems and methods for using computing system application data to determine neurotransmitter levels in a subject and determining activities that if performed by the subject can increase determined deficiencies in neurotransmitter levels.

BACKGROUND OF THE DISCLOSURE

Mental health has become increasingly recognized as something that should be cared for with as much concern as physical health. Today, it is estimated that more than 80% of the worldwide population are burdened by depression, anxiety or addiction. This erosion of mental health has consequential implications for society at large. Mental health issues can be attributed to increases in crime, suicide rates, and even loss of productivity. Thus, improving mental health across a population not only confers benefits to the individual whose mental health is improved, but also benefits society.

Recognizing the importance of mental health, many approaches to improving mental health have been suggested and applied. For instance, philosophical, psychological, technical, and neuroscientific approaches to improving mental health have been implemented with mixed success. Many of these approaches have failed or provided marginal improvements in mental health. One reason for these shortcomings is that it can be difficult to obtain data that can provide a window into the mental health of an individual. Often, acquiring such data can require the individual to submit to extensive and time consuming counseling sessions with a therapist to assess issues. An individual may only subject themselves to such an examination when an issue with mental health arises. However, in terms of prevention, there is not a non-intrusive and meaningful way of tracking indicators of mental health on a daily basis. Another reason for the shortcomings may be attributed to the fact that many approaches while diagnosing mental health issues, may not provide meaningful suggestions on a daily basis for improving mental health. Even if suggestions are provided, those suggestions may not be individually tailored to the specific patient, but instead just provide general guidance for improving mental health, which may or may not improve the specific causes of decreased mental health.

Mobile computing devices such as mobile phones can provide a great deal of data regarding the mental health of an individual. For instance, digital data such as calendar entries, phone calls, text messages, and other application data can provide insight into the type of activities that an individual is engaging in on a daily basis, and thus may be useful in determining whether an individual is engaging in the sorts of activities that will benefit their mental health and ensure that it remains healthy. Mobile devices are constantly following an individual (in a pocket or purse for example) and can be utilized to provide the necessary information about a user's daily activities that can be used to generate an overall mental health assessment without requiring intrusive psychological diagnostic techniques. As an example, calendar entries on a mobile device can provide insight as to the types of activities that a user is engaging in, and an analysis of those activities can indicate whether the user is performing activities in their daily life that promote mental health, for instance, by causing the brain to release certain neurotransmitters known to promote overall happiness.

What is needed is a system that can acquire mobile device information and data associated with a user's daily activities, and translate that data into a meaningful analysis of whether the user is maintaining a healthy lifestyle (from a mental health standpoint). Furthermore, rather than simply providing an assessment of whether or not the user is engaging in activities that will promote the overall mental health of the individual, but what is also needed is a system that can use the assessment to the provide the user with guidance as to how to modify their daily routines to ensure that they are able to fully realize peak happiness.

SUMMARY OF THE DISCLOSURE

Accordingly, provided herein are systems and methods for evaluating and improving neurotransmitter levels based on mobile device application data. In one or more examples, the system can be implemented as a computing application that is configured to download information from a user's mobile device that can provide insight into the user's daily mental health. Once the data is acquired, in one or more examples, the application can prompt the user to provide additional information regarding data acquired from the mobile device, and using both the user's input and the acquired data, the application can calculate neurotransmitter activity in the user and identify any deficiencies in neurotransmitter activity.

In addition to analyzing neurotransmitter levels in a user and identifying deficits in neurotransmitter activity, in one or more examples, the application can use the data to determine what a user's ideal levels of neurotransmitters should be and provide suggestions to the user as to the types of activities and behaviors that they could engage in to improve the neurotransmitter levels so as to fully realize their individual potential for happiness.

According to an aspect, a method for assessing neurotransmitter levels of a user based on a user's activity data stored on a computing device includes: receiving data from a computing device associated with the user, wherein the received data is associated with one or more activities performed by the user; displaying a first graphical user interface at the display, wherein the first graphical user interface is configured to display and receive one or more categorizations of the one or more activities performed by the user from the user; determining one or more emotions based on the received one or more categorizations of the one or more activities performed by the user; displaying a second graphical user interface at the display, wherein the second graphical user interface is configured to receive one or more quantitative ratings corresponding to each of the determined one or more emotions from the user; determining one or more neurotransmitter activity levels of the user based on the received one or more quantitative ratings received from the user; determining one or more optimal neurotransmitter activity levels; determining one or more neurotransmitter deficiencies of the user, based on the determined one or more neurotransmitter activity levels of the user and the determined one or more optimal neurotransmitter activity levels; determining one or more neurotransmitter deficiencies of the user, based on the determined one or more neurotransmitter activity levels of the user and the determined one or more optimal neurotransmitter activity levels; and generating and display one or more suggestions for increasing the determined one or more neurotransmitter activity levels.

Optionally, the method comprises displaying a third graphical user interface at the display, wherein the third graphical user interface is configured to display the determined one or more optimal neurotransmitter activities and the determined one or more neurotransmitter deficiencies.

Optionally, the third graphical user interface includes one or more user selectable features that when selected by the user allows the user to add an event corresponding to the one or more generated suggestions to an electronic calendar associated with the user.

Optionally, the generated one or more suggestions for increasing the determined one or more neurotransmitter are generated by selecting one or more entries from a database containing a plurality of suggestions for increasing neurotransmitter levels.

Optionally, the database containing a plurality of suggestions for increasing neurotransmitter levels is categorized based on one or more types of neurotransmitters.

Optionally, the database containing a plurality of suggestions for increasing neurotransmitter levels is categorized based on an amount of increase in the neurotransmitter levels needed.

Optionally, the categorizations received from the user comprises at least one category selected from the group consisting of: work and school, consumption, leisure, social, community service, religious, and spiritual.

Optionally, the determined one or more emotions comprises at least one emotion selected from the group consisting of: enthusiasm, sexual desire, pride, nurturant love, contentment, amusement, attachment love, pleasure, and gratitude.

Optionally, determining the one or more neurotransmitter activity levels of the user includes applying the received one or more quantitative ratings received from the user to a positive emotion to neurotransmitter (PE-NT) matrix.

Optionally, the second graphical user interface is configured to receive one or more lengths of time of the one or more activities performed by the user and determining the one or more neurotransmitter activity levels of the user includes applying the received one or more lengths of time of the one or more activities to the PE-NT matrix.

Optionally, the one or more neurotransmitter activity levels include one or more levels associated with: dopamine, testosterone, serotonin, oxytocin, cannabinoids, and opioids.

Optionally, determining one or more emotions based on the received one or more categorizations of the one or more activities performed by the user is based on a behavior-to-positive emotion (B-PE) matrix.

Optionally, the method comprises determining an overall return on happiness (ROH) score based on the determined one or more neurotransmitter activity levels.

Optionally, the method comprises determining an optimal ROH score.

Optionally, the method comprises determining one or more ROH score deficiencies of the user, based on the determined ROH score and the determined optimal ROH score.

According to an aspect, a system for assessing neurotransmitter levels of a user based on a user's activity data stored on a computing device includes: a memory; a display; one or more processors; an one or more programs, wherein the one or more programs are stored in the memory and configured to be executed by the one or more processors, the one or more programs when executed by the one or processors cause the processor to: receive data from a computing device associated with the user, wherein the received data is associated with one or more activities performed by the user; display a first graphical user interface at the display, wherein the first graphical user interface is configured to display and receive one or more categorizations of the one or more activities performed by the user; determine one or more emotions based on the received one or more categorizations of the one or more activities performed by the user; display a second graphical user interface at the display, wherein the second graphical user interface is configured to receive one or more quantitative ratings corresponding to each of the determined one or more emotions from the user; determine one or more neurotransmitter activity levels of the user based on the received one or more quantitative ratings received from the user; determine one or more optimal neurotransmitter activity levels; determine one or more neurotransmitter deficiencies of the user, based on the determined one or more neurotransmitter activity levels of the user and the determined one or more optimal neurotransmitter activity levels; and generate and display one or more suggestions for increasing the determined one or more neurotransmitter activity levels.

Optionally, the processor is further caused to display a third graphical user interface at the display, wherein the third graphical user interface is configured to display the determined one or more optimal neurotransmitter activities and the determined one or more neurotransmitter deficiencies.

Optionally, the third graphical user interface includes one or more user selectable features that when selected by the user allows the user to add an event corresponding to the one or more generated suggestions to an electronic calendar associated with the user.

Optionally, the generated one or more suggestions for increasing the determined one or more neurotransmitter are generated by selecting one or more entries from a database containing a plurality of suggestions for increasing neurotransmitter levels.

Optionally, the database containing a plurality of suggestions for increasing neurotransmitter levels is categorized based on one or more types of neurotransmitters.

Optionally, the database containing a plurality of suggestions for increasing neurotransmitter levels is categorized based on an amount of increase in the neurotransmitter levels needed.

Optionally, the categorizations received from the user comprises at least one category selected from the group consisting of: work and school, consumption, leisure, social, community service, religious, and spiritual.

Optionally, the determined one or more emotions comprises at least one emotion selected from the group consisting of: enthusiasm, sexual desire, pride, nurturant love, contentment, amusement, attachment love, pleasure, and gratitude.

Optionally, determining the one or more neurotransmitter activity levels of the user includes applying the received one or more quantitative ratings received from the user to a positive emotion to neurotransmitter (PE-NT) matrix.

Optionally, the second graphical user interface is configured to receive one or more lengths of time of the one or more activities performed by the user and determining the one or more neurotransmitter activity levels of the user includes applying the received one or more lengths of time of the one or more activities to the PE-NT matrix.

Optionally, the one or more neurotransmitter activity levels include one or more levels associated with: dopamine, testosterone, serotonin, oxytocin, cannabinoids, and opioids.

Optionally, determining one or more emotions based on the received one or more categorizations of the one or more activities performed by the user is based on a behavior-to-positive emotion (B-PE) matrix.

Optionally, the processor is further caused to determine an overall return on happiness (ROH) score based on the determined one or more neurotransmitter activity levels.

Optionally, the processor is further caused to determine an optimal ROH score.

Optionally, the processor is further caused to determine one or more ROH score deficiencies of the user, based on the determined ROH score and the determined optimal ROH score.

According to an aspect, a non-transitory computer readable storage medium storing one or more programs comprising instructions for assessing neurotransmitter levels of a user based on a user's activity data stored on a computing device, which, when executed by an electronic device with a display, cause the device to: receive data from a computing device associated with the user, wherein the received data is associated with one or more activities performed by the user; display a first graphical user interface at the display, wherein the first graphical user interface is configured to display and receive one or more categorizations of the one or more activities performed by the user from the user; determine one or more emotions based on the received one or more categorizations of the one or more activities performed by the user; display a second graphical user interface at the display, wherein the second graphical user interface is configured to receive one or more quantitative ratings corresponding to each of the determined one or more emotions from the user; determine one or more neurotransmitter activity levels of the user based on the received one or more quantitative ratings received from the user; determine one or more optimal neurotransmitter activity levels; determine one or more neurotransmitter deficiencies of the user, based on the determined one or more neurotransmitter activity levels of the user and the determined one or more optimal neurotransmitter activity levels; determine one or more optimal neurotransmitter activity levels; determine one or more neurotransmitter deficiencies of the user, based on the determined one or more neurotransmitter activity levels of the user and the determined one or more optimal neurotransmitter activity levels; and generate and display one or more suggestions for increasing the determined one or more neurotransmitter activity levels.

Optionally, the device is further caused to display a third graphical user interface at the display, wherein the third graphical user interface is configured to display the determined one or more optimal neurotransmitter activities and the determined one or more neurotransmitter deficiencies.

Optionally, the third graphical user interface includes one or more user selectable features that when selected by the user allows the user to add an event corresponding to the one or more generated suggestions to an electronic calendar associated with the user.

Optionally, the generated one or more suggestions for increasing the determined one or more neurotransmitter are generated by selecting one or more entries from a database containing a plurality of suggestions for increasing neurotransmitter levels.

Optionally, the database containing a plurality of suggestions for increasing neurotransmitter levels is categorized based on one or more types of neurotransmitters.

Optionally, the database containing a plurality of suggestions for increasing neurotransmitter levels is categorized based on an amount of increase in the neurotransmitter levels needed.

Optionally, the categorizations received from the user comprises at least one category selected from the group consisting of: work and school, consumption, leisure, social, community service, religious, and spiritual.

Optionally, the determined one or more emotions comprises at least one emotion selected from the group consisting of: enthusiasm, sexual desire, pride, nurturant love, contentment, amusement, attachment love, pleasure, and gratitude.

Optionally, determining the one or more neurotransmitter activity levels of the user includes applying the received one or more quantitative ratings received from the user to a positive emotion to neurotransmitter (PE-NT) matrix.

Optionally, the second graphical user interface is configured to receive one or more lengths of time of the one or more activities performed by the user and determining the one or more neurotransmitter activity levels of the user includes applying the received one or more lengths of time of the one or more activities to the PE-NT matrix.

Optionally, the one or more neurotransmitter activity levels include one or more levels associated with: dopamine, testosterone, serotonin, oxytocin, cannabinoids, and opioids.

Optionally, determining one or more emotions based on the received one or more categorizations of the one or more activities performed by the user is based on a behavior-to-positive emotion (B-PE) matrix.

Optionally, the processor is further caused to determine an overall return on happiness (ROH) score based on the determined one or more neurotransmitter activity levels.

Optionally, the processor is further caused to determine an optimal ROH score.

Optionally, the processor is further caused to determine one or more ROH score deficiencies of the user, based on the determined ROH score and the determined optimal ROH score.

BRIEF DESCRIPTION OF THE FIGURES

FIG. 2 illustrates exemplary graphical user interfaces configured to receive user input regarding activities acquired from a user's mobile device according to examples of the disclosure.

FIG. 3 illustrates an exemplary behavior-to-positive emotion matrix according to examples of the disclosure.

FIG. 7 illustrates other exemplary graphical user interface configured to display neurotransmitter levels associated with an activity acquired from a user's mobile device according to examples of the disclosure.

FIGS. 11A-C illustrate an exemplary database of suggestions for activities based on ROH and individual neurotransmitter levels according to examples of the disclosure.

FIGS. 12A-C illustrate another exemplary database of suggestions for activities based on ROH and individual neurotransmitter levels according to examples of the disclosure.

FIGS. 13A-B illustrate an exemplary database of suggestions for activities based on ROH and individual neurotransmitter levels according to examples of the disclosure.

FIG. 17 illustrates the attrition and number of participants/users during the ROH test over time and the retention rates according to examples of the disclosure.

DETAILED DESCRIPTION OF THE DISCLOSURE

Figure 1:
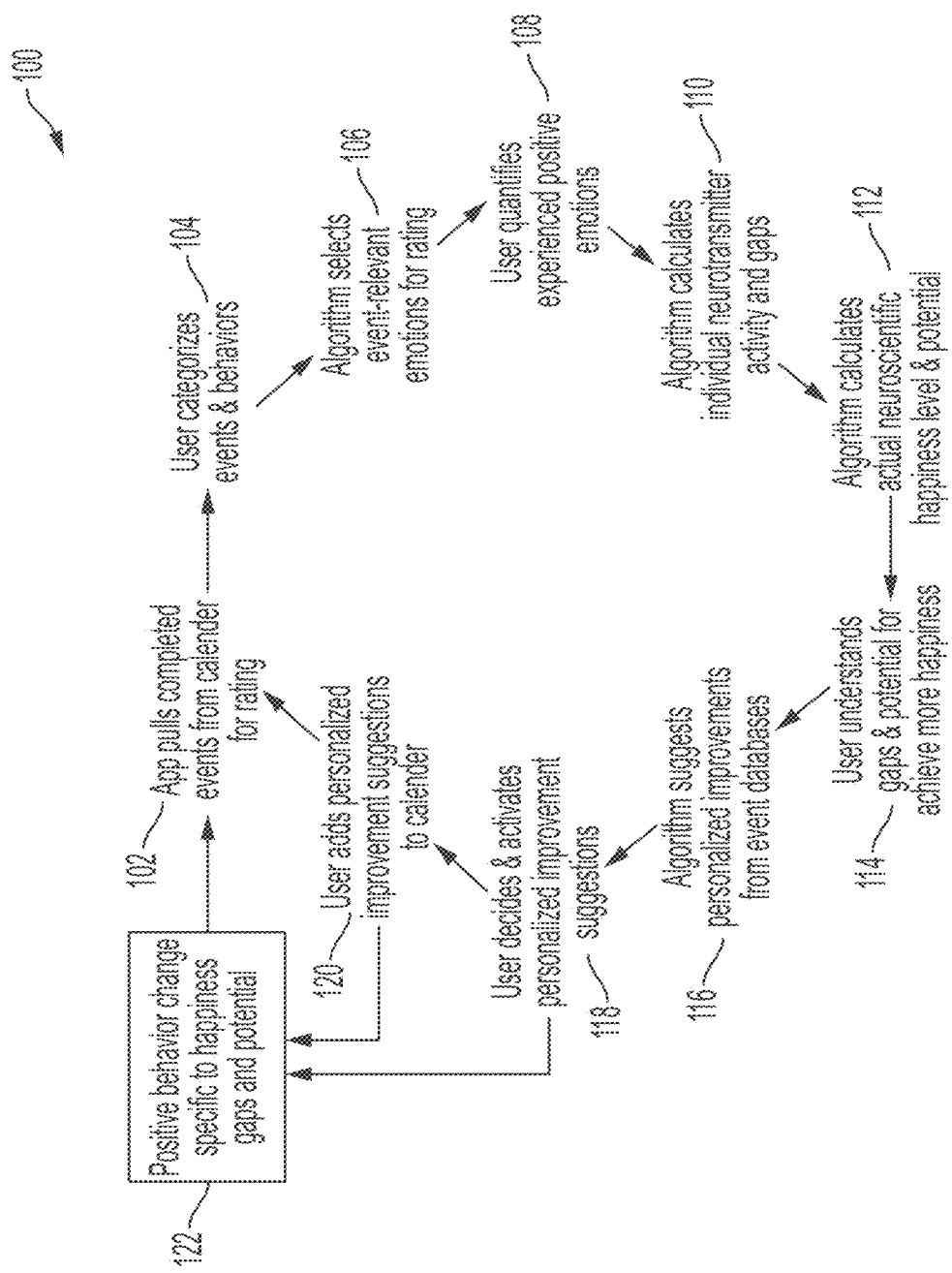
FIG. 1 illustrates an exemplary process for determining neurotransmitter levels based on data received for a computing device and providing suggestions to improve levels based on the received data according to examples of the disclosure.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a," "an," and "the" used in the following description are intended to include the plural forms as well unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices without loss of generality.

However, all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

Certain aspects of the present Disclosure include process steps and instructions described herein in the form of an algorithm. It should be noted that the process steps and instructions of the present Disclosure could be embodied in software, firmware, or hardware, and, when embodied in software, they could be downloaded to reside on and be operated from different platforms used by a variety of operating systems.

The present disclosure also relates to a device for performing the operations herein. This device may be specially constructed for the required purposes or it may comprise a general-purpose computer selectively activated or reconfigured by a computer program stored in the computer. Such a computer program may be stored in a non-transitory, computer-readable storage medium such as, but not limited to, any type of disk, including floppy disks, optical disks, CD-ROMs, magnetic-optical disks, read-only memories (ROMs), random access memories (RAMs), EPROMs, EEPROMs, magnetic or optical cards, application-specific integrated circuits (ASICs), or any type of media suitable for storing electronic instructions and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present disclosure is not described with reference to any particular programming language. It will be appreciated that a variety of programming languages may be used to implement the teachings of the present disclosure as described herein.

Human interaction with computing devices has expanded and diversified over the years such that computing devices can now provide a window into the daily lives of their users. For instance, with respect to mobile devices, user's interactions with the mobile device can provide a window into what a user is doing during the day at any particular moment in time. Mobile device users often engage with digital calendars to schedule appointments, use various applications stored on the mobile device for purposes of entertainment or information gather, and can even use mobile device to make contact with friends, family, or other individuals via telephone calls and text messages.

The activities that an individual engages in during the day can have a substantial impact on their overall happiness. Happiness can be measured by certain neuroscientific and psychological biomarkers that are present in the human body at any given moment of time. For instance certain neurotransmitters in the brain such as dopamine, testosterone, serotonin, oxytocin, cannabinoids, and opioids, can have a substantial impact on the overall mental health and happiness of an individual. Maintaining a certain level of each neurotransmitter throughout the day can lead to an overall improvement in mental health and can ensure that an individual is realizing their maximum happiness potential.

The amount of neurotransmitters in our bodies can be correlated with the activities we engage in on a daily basis. For instance, engaging in positive and pleasurable activities can correlate with the release of neurotransmitters in our system tied with positive mental health and happiness. However, achieving happiness or peak mental health does not simply mean to increase the amount of neurotransmitters in our body. Instead, peak mental health and happiness can correlate with achieving and maintaining a certain ratio or combination of neurotransmitters in our body throughout the day. The activities that an individual engages in can increase certain neurotransmitter levels, while having substantially no effect on others. Thus, in order to achieve the right combination of neurotransmitters correlated with peak happiness, first an individual must have a way to understand what their neurotransmitter levels are at any given point in time, must be able to determine what neurotransmitters need to be boosted in order to reach peak mental health, and must also know what type of activities they need to engage in to achieve an optimal balance between the neurotransmitters.

In one or more examples of the disclosure, the data generated from a computing device that is used by an individual can be leveraged to provide measurements of neurotransmitter levels in the body. As described in detail below, by analyzing the data from a mobile device, the systems and methods described herein can provide an estimate of the neurotransmitter levels produced in the body at any given moment in time. The estimate can then be used to identify any potential gaps in neurotransmitter levels, and in one or more examples, the system can provide suggestions for activities that will help the individual to eliminate those gaps therefore realizing an optimal combination of neurotransmitter levels that can achieve peak mental health.

FIG. 1 illustrates an exemplary process for determining neurotransmitter levels based on data received for a computing device and providing suggestions to improve levels based on the received data according to examples of the disclosure. In one or more examples of the disclosure, the process 100 described with respect to FIG. 1 can be implemented on a computing device such as a mobile computing device like a mobile phone, as an application that is installed on the computing device.

In one or more examples, the process 100 can begin at step 102 wherein the application installed on the mobile computing device can download information from other applications or functionalities installed on the mobile computing device pertaining to a user's daily activities. For instance, in one or more examples, the application can access a calendar stored on the computing device to obtain information regarding activities that the user engaged in during a given day or time period. In one or more examples, the downloaded information can also include telephone calls, text messages and other data stored on the mobile device that can indicate what the user was doing at any given time during the time period. In one or more examples, the digital data can include the amount of screen time of the user as well as the use of various "lifestyle" applications. In one or more examples, in addition to pulling information (i.e., digital data) from the calendar itself, in one or more examples and at step 102, additional information can be gathered from both the user and their device to supplement the information pulled from the user's calendar. For instance, in one or more examples, geolocation information, weather data, and tagging information to other individual's location or movement can be extracted from the user's computing device (i.e., mobile phone) and included with the calendar information. Alternatively or additionally, in one or more examples, biodata can also be extracted from one or more wearable devices of the user (i.e., watch or personal fitness tracker). In one or more examples, a user can be prompted to add a manual link to the personal contact information of a person or persons involved in the event. Upon the completion of the event, the user can further be prompted to add data about the event to the information pulled from the user's calendar. For instance, the use can be prompted to add one or more photos associated with the event to promote later recall of the event. Furthermore, and as discussed below, a user can also be prompted to add one or more event-specific "hashtags" i.e., words or phrases associated with the event to further enhance their recall of the event once the event is over.

In one or more examples, in addition to pulling calendar or other device data to extract events that may be related to a user's happiness, the user can instead be presented with a graphical user interface (i.e., a button or series of buttons) that they can instantaneously interact with to capture unplanned moments of emotional significance that otherwise might be lost for emotional rating. For instance, in one or more examples, the user can be presented with a graphical "button" (either on the mobile phone's lock screen or as a button on a desktop) that the user can press to capture an event that occurs during the day of emotional significance. In one or more examples, when the button is pressed, the time and location stamp can be immediately stored. In one or more examples, while the location and time stamp can be automatically obtained upon pushing a button, the information can be further complemented by automated tags to an individual's location data or the user can be prompted to add hashtags on their own, allowing them to later recall the event when rating it for ROH purposes. In one or more examples, the events recorded in this manner can be presented to the user in a substantially similar manner to calendared events for full rating and data entry.

In one or more examples, and alternatively or additionally to pressing a button as described above, the user can initiate the recording of an event of emotional significance using other methods. For instance, in one or more examples, the user can initiate a recording of an event by take a photograph or series of photographs, and then linking the one or more photographs as an event for later rating as described above. Alternatively or additionally, the user can create a "hashtag" (i.e., a word or phrase) that can signify or be associated with a contemporaneous event for later rating as described above. Alternatively or additionally, the user upon pushing a button as described above, can be presented with a plurality of emoji's representing different emotions (for instance the nine emotions described further below) for selection of one key emotion of interest to be captured as a reminder during later rating. In this way, rather than simply using calendar entries to signify events during the day, the user can create their own events "on the fly" and provide visual or textual associations with those events so that they can be later rated by the user in substantially the same manner as event captured by the user's calendar on a mobile device.

In one or examples, the mere existence of an activity on a user's mobile computing device may not be enough information to accurately assess neurotransmitter levels in the human, thus after downloading the digital data at step 102, the process 100 can move to step 104 wherein the user may be presented with one or more graphical user interfaces asking them to categorize each event and behavior (described in detail below) downloaded by the application. In one or more examples, downloaded events can be portrayed to the user in a "Rating" tap system, in which the user can categorize the events based on a plurality of categories that can be neurologically distinguished. In one or more examples of the disclosure, once a calendar event is completed, the user may be presented with a short notification via a graphical user interfaced from the application indicating that rating for the particular past event can be started.

In one or more examples, the notifications can be structured to promote memory creation by promoting events from an individual's short-term memory to their long-term memory. In one or more examples, the user can be initially sent a notification immediately after the completion of an event (as described above) for example by asking the user how the even contributed to their happiness. Additionally, or alternatively, the user can also be sent a notification in the evening before their bed time (for instance at 10 pm) that allows them to rate their top events of the day. In this way, the notification before going to bed can allow for the user to refresh their short-term memory (i.e., events that happened in the day) in the prefrontal cortex for events with highest emotional significance thus enhancing the transfer from the prefrontal cortex (i.e., short-term memory) to the neocortex (i.e., long-term memory) when the user is sleeping (when the body transfers memories from short-term to long-term memory).

Additionally, in one or more examples, the user can have the option of adding a calendar in order to capture any unplanned or spontaneous events that occurred and should be added. After adding a past event, the user can be prompted to rate the event as described in detail below. As described in further detail below, the categories presented to the user can be designed as a first filter for upcoming emotion ratings (described in further detail below).

FIG. 2 illustrates exemplary graphical user interfaces configured to receive user input regarding activities acquired from a user's mobile device according to examples of the disclosure. In one or more examples, the graphical user interfaces 200 can include a first graphical user interface that is configured to accept input from a user regarding whether or not the user wishes to rate the event. In one or more examples, the graphical user interface 202 can ask the user whether or not they wish to rate a particular event or simply ignore the event. In one or more examples, the user may choose to ignore an even if the event did not take place (even though it may have been calendared). Events that are ignored may not be included in the calculation of neurotransmitter levels. However, events that the user chooses to rate may be included as part of the calculation and determination of neurotransmitter levels at a given moment in time.

In one or more examples, the graphical user interface 202 can include one or more user selectable buttons 206 and 208. In one or more examples, user selectable button 206 when selected by a user, can indicate to the application that the user wishes to ignore an event downloaded by the application. In one or more examples, user selectable button 208 when selected by a user, can indicate to the application that the user wishes to rate the event and include the event as part of the calculation of neurotransmitter levels.

In one or more examples if a user selects button 208, then the user can be presented with graphical user interface 204 wherein the user is asked to categorize the event based on one or more categories. For instance, in one or more examples, and as illustrated in graphical user interface 204, the user may be asked to categorize an event based on seven categories: (1) Work & School, (2) Consumption, (3) Leisure, (4) Social, (5) Community Service, (6) Religious, and (7) Spiritual. Each of the categories provided above are meant as examples only and should not be seen as limiting to the disclosure. Alternative or additional categories could be included, for instance, alternatively or additionally to the list provided above, the categories could include: (1) Biological Basics, (2) Work, (3) Learning, (3) Consumption, (4) Leisure, (5) Family, (6) Partner/Friends, (8) Taking Care of Others, and (9) Spiritual. The event categories can be configured to cover all potential events and behaviors of human life that can be neurologically distinguished, and can provide a first filter for upcoming emotion ratings (described in further detail below).

In one or more examples, once the user categorizes an event using graphical user interface 204, they can be presented with an additional graphical user interface 210, which can be configured to prompt the user to further categorize the event. In one or more examples of the disclosure, the "subcategories" presented in graphical user interface 210 can act as "emotion gatekeepers" and can be compiled in order to predefine which positive emotions can and cannot be triggered neuroscientifically. For example, playing with friends can trigger attachment love but not nurturant love. Hugging your kids can trigger nurturant love but not sexual desire. Participating in sports can trigger pleasure but not amusement. Thus, the subcategories provided by graphical user interface 210 and which are selectable by the user can ensure that only the proper types of emotions are evaluated as they pertain to a certain event. In one or more examples, the subcategories can be omitted altogether and instead a user can simply provide a "hashtag" specifier, in which the user can manually specify further information on the behavior or event experienced. Such additional information can help the recall process in the future. In one or more examples, the graphical user interface 204 can allow for the user only to select main categories (while omitting any subcategories) or can allow for the user to select a subset of the main categories and subcategories.

Returning to the example of FIG. 1, once the user categorizes events and behaviors at step 104, the process 100 can move to step 106 wherein the application determines event-relevant emotions for rating by the user. In one or more examples, the application can use the event categorizations provided the user to filter event-relevant positive emotions for further rating by a user. As an example, the event-relevant positive emotions can include: (1) Enthusiasm, (2) Sexual Desire, (3) Pride/Recognition, (4) Nurturant Love, (5) Contentment, (6) Amusement, (7) Attachment Love, (8) Pleasure, and (9) Gratitude. The event-positive emotions listed above are meant as examples only and should be seen as limiting to the disclosure. In one or more examples, the above list can be modified with different emotions, and/or emotions from the above list can be removed.

In one or more examples of the disclosure, the process of allocating behaviors of a user to emotions (i.e., the nine emotions listed above) can be based on a behavior-to-positive emotion matrix. FIG. 3 illustrates an exemplary behavior-to-positive emotion (B-PE) matrix according to examples of the disclosure. In one or more examples, the B-PE matrix 300 of FIG. 3 can be configured and utilized to allocate behaviors to emotions. Based on the categorization of behaviors provided by the user at step 104 of FIG. 1, the B-PE matrix can be used to determine what emotions each behavior may elicit. In one or more examples, and based on the B-PE matrix 300 of FIG. 3, the user can be prompted to rate how intensely they felt each emotion indicated by the B-PE matrix 300 (described in further detail below.) In the B-PE matrix 300 of FIG. 3, each "1" indicated can mean that the corresponding emotion should be selected for emotion rating, whereas a "0" can indicate that the corresponding emotion is not associated with the behavior.

In one or more examples, the rows of the B-PE matrix can indicate one or more behaviors as categorized at step 104 of FIG. 1. The columns can relate to one of the nine neurologically possible emotions: (1) Enthusiasm (EN), (2) Sexual Desire (SD), (3) Pride/Recognition (PR), (4) Nurturant Love (NL), (5) Contentment (CO), (6) Amusement (AM), (7) Attachment Love (AL), (8) Pleasure (PL), and (9) Gratitude (GR).

To illustrate how the B-PE Matrix can be configured, take the example of "Work," which is a behavior that many adults engage in on a daily basis. If at step 104 of FIG. 1, an activity performed by a user based on the digital downloaded by the application is categorized by the user as being "work," then turning to the B-PE matrix 300, that behavior can be correlated with six different emotions: Enthusiasm, Pride/Recognition, Contentment, Attachment Love, Pleasure, and Gratitude. Based on the B-PE matrix 300, the emotions of sexual desire, Nurturant love, and Amusement, will not be determined to be indicated by a work activity. As described in further detail below, each indicated emotion indicated by a particular behavior categorized by a user at step 104 of FIG. 1 can be "selected" for further emotional rating as discussed in further detail below.

Returning to the example of FIG. 1, once the application using the B-PE matrix of FIG. 3 selects event-relevant emotions for rating at step 106, the process 100 can move to step 108 wherein the user is presented with one or more graphical user interfaces configured to prompt the user to quantify experienced positive emotions associated with the behaviors and events categorized at step 104. By having the user quantify the positive emotions felt while engaging in a particular behavior, the application can use the quantification to determine a level of neurotransmitter estimated to have been caused by the event.

Figure 4:
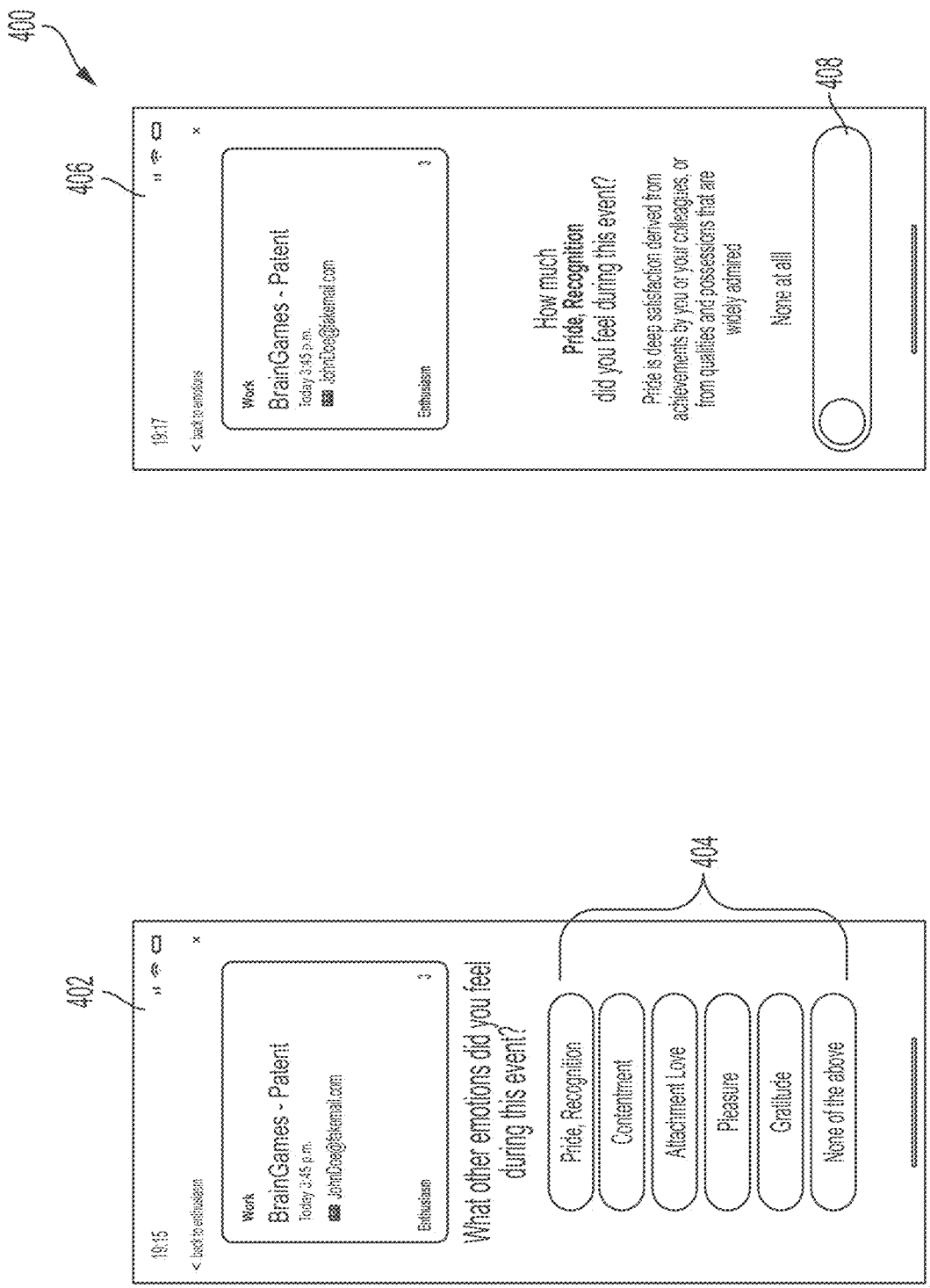
FIG. 4 illustrates exemplary graphical user interfaces configured to acquire a user's input regarding their emotions during one or more activities acquired from a user's mobile device according to examples of the disclosure.

FIG. 4 illustrates exemplary graphical user interfaces configured to acquire a user's input regarding their emotions during one or more activities acquired from a user's mobile device according to examples of the disclosure. In the example of FIG. 4, the graphical user interfaces 400 can include a first graphical user interface 402 configured to prompt the user to identify the emotions they felt during a particular event. The emotions 404 presented to the user in graphical user interface 402 can be based on the emotions identified by the B-PE matrix described above with respect to FIG. 3.

In the example of graphical user interface 402, the event "BrainGames-Patent" (i.e., a work-related meeting) can be associated with Pride/Recognition, Contentment, Attachment Love, Pleasure, and Gratitude. In one or more examples, the user can select one of the emotions 404 that were felt during the event. In one or more examples, the emotions 404 can be displayed as user selectable buttons that when selected by the user can cause the application to display a second graphical user interface 406 that allows the user to quantify the emotion selected. For example, if at graphical user interface 402 the user indicates that they felt pride/recognition during the "BrainGames Patent" event, then the application can present the user with graphical user interface 406 which can be configured to prompt the user to quantify how much pride/recognition they felt at the event.

In one or more examples, graphical user interface 406 can include a slide bar 408 that can allow the user to quantify the amount of a particular emotion felt. In one or more examples, the slide bar 408 when slid to the left (which can be the default) can indicate that the user felt no sense of pride/recognition from the event. The user can slide the slide bar 408 further to the right based on the level of the emotion they felt, and the position of the slide bar can be proportional to the amount of the emotion felt. Thus, if the user slides the slide bar 408 all the way to the right, that can indicate that the user felt the maximum sense of pride/recognition that was possible.

The slide bar 408 is meant only as an example and should not be seen as limiting. In one or more examples, an alternative method of soliciting the user to quantify the emotion felt can be used. For instance, the user could be asked to provide a number 1 to 10 to quantify the amount of an emotion felt with 1 indicating no emotion felt and 10 indicating the highest amount. Thus, in one or more examples, the slide bar 408 can allow for the user to provide a continuous free-flowing quantification of the emotion, whereas alternatively or additionally they can provide the graphical user interface with a discrete level of emotion (i.e., an integer value from 0 to 8). In one or more examples, after indicating the amount of the emotion at graphical user interface 406, the user can be sent back to graphical user interface 402 to quantify additional emotions, and the process can repeat. The process of going back and forth between graphical user interface 402 and 406 can repeat until all the emotions identified at 404 of graphical user interface 402 are quantified.

In one or more examples, the application can limit the time that a user has to quantify the emotion. Recognizing that emotion ratings by users can be highly precise when the retrieval of the rating is executed very fast (i.e., 3-5 seconds), the application can limit the amount of time that the user has to quantify the emotion felt. This limitation can prevent the user from further rumination excluding subconscious retrieval manipulation. Additionally, in one or more examples, the user can be prompted to indicate the duration of the emotion/event.

Returning to the example of FIG. 1, once the user has quantified the experienced positive emotions at step 108, the process 100 can move to step 110 wherein the application can determine individual neurotransmitter activity and gaps. In one or more examples, at step 110, and using the quantification of emotions provided by the user at step 108, the application can calculate and/or estimate the level of the neurotransmitters (such as dopamine, testosterone, serotonin, oxytocin, cannabinoids, and opioids described above) associated with a particular event. The calculation performed by the application can be expressed to the user of the application by providing a display to the user that shows the amount of each neurotransmitter associated with a particular event.

Figure 5:
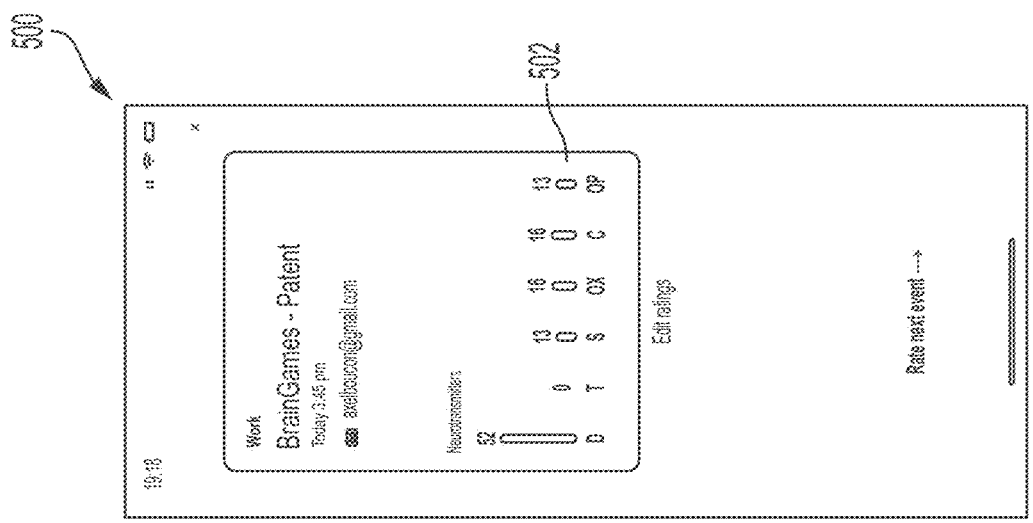
FIG. 5 illustrates an exemplary graphical user interface configured to display neurotransmitter levels associated with an activity acquired from a user's mobile device according to examples of the disclosure.

FIG. 5 illustrates an exemplary graphical user interface configured to display neurotransmitter levels associated with an activity acquired from a user's mobile device according to examples of the disclosure. In the example of FIG. 5, the graphical user interface 500 can be configured to provide the user with a bar graph 502 that shows the levels of each of the neurotransmitters associated with a particular event. In the example of FIG. 5, and particularly the "BrainGames Patent" event, the bar graph 502 can illustrate that dopamine was at level 52 as a result of the event, testosterone was 0, Serotonin was at 13, Oxytocin was at 16, Cannabinoids was at 16 and Opioids was at 13.

To calculate the amount of each neurotransmitter, the application can utilize at positive emotion to Neurotransmitter (PE-NT) matrix that can translate the quantified positive emotions derived at step 108 into an amount of each of the neurotransmitters associated with positive emotions. The calculation can be based on the user quantification provided at step 108 as well as the amount of time that each event took.

Figure 6:
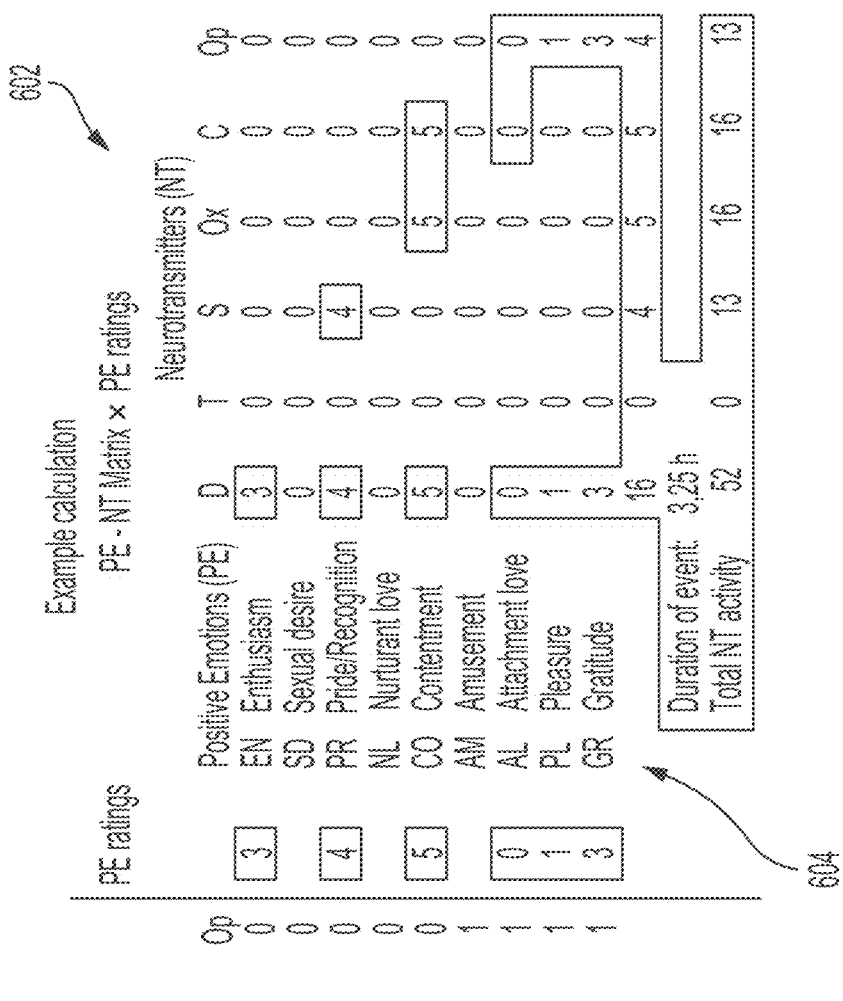
FIG. 6 illustrates an exemplary neurotransmitter level calculation pertaining to a particular activity acquired from a user's mobile device according to examples of the disclosure.

FIG. 6 illustrates an exemplary neurotransmitter level calculation pertaining to a particular activity acquired from a user's mobile device according to examples of the disclosure. FIG. 6. Illustrates an exemplary PE-NT matrix 602 that can be used to calculate the amount of a particular neurotransmitter. The rows of the PE-NT matrix 602 can represent the emotion categories such as enthusiasm, sexual desire, pride/recognition, nurturant love, contentment, amusement, pleasure, and gratitude. The columns of the PE-NT matrix 602 can represent the neurotransmitters (dopamine, testosterone, Serotonin, Oxytocin, Cannabinoids, and Opioids) associated with positive emotions. A "1" in the matrix can indicate that a particular neurotransmitter is associated with that particular emotion. A "0" in the matrix can indicate that a particular is not associated with that particular emotion.

The PE-NT matrix 602 can be used to calculate the amount of a neurotransmitter associated with an activity. Calculation 604 illustrates an exemplary calculation. In one or more examples, the calculation 604 can include a PE ratings column that shows the ratings provided by the user at step 108 of FIG. 1. For instance, using the "BrainGames Patent" example, the user may have rated their enthusiasm during the event as mild (indicating that its lower than average but still present) and so that rating can be quantified as a 3. In the same example, in the PE ratings column the user may rate their contentment as a 5 which is average. In order to calculate the amount of neurotransmitter, the calculation can multiply the rating by the PE-NT matrix to generate a number associated with the amount of a particular neurotransmitter. For instance, as shown in PE-NT matrix 602, enthusiasm can be associated with the release of dopamine. Looking at calculation 604, the PE rating for enthusiasm (provided by the user) is 3. That value is multiplied by 1 under the dopamine column to arrive at a value of 3. Thus, with respect to the enthusiasm felt by the user as expressed in the PE rating, the dopamine level associated with that enthusiasm is quantified at 3. In one or more examples, the remaining columns are left at 0 because those neurotransmitters are not associated with enthusiasm.

In one or more examples, each and every positive emotion can be multiplied by the PE rating to arrive at a value for each neurotransmitter. For instance, contentment was rated 5 by the user, and thus since contentment is associated with dopamine, oxytocin, and cannabinoids, each of those elements can be set at 5 (multiplying 5×1). Once the calculate is made for each emotion at each neurotransmitter, the calculation can add up the totals for each neurotransmitter. Turning to the example calculation 604 of FIG. 6, for dopamine, the dopamine levels for each emotion can add up to 16. For serotonin, the calculation can add up to 4 and so on and so forth for each neurotransmitter.

Once each neurotransmitter is tallied up, each tally can be multiplied the duration of the event to determine the total neurotransmitter activity associated with the event. Using the example of dopamine, the tally added up to 16 (as described above) and that tally can be multiplied by 3.25 (i.e., 3.25 hours which was the time indicated by the user that the event lasted) to come to a total of 52 for dopamine. Each individual level for each neurotransmitter can be similarly calculated.

As described above, the user can be presented with one or more graphical user interfaces to visually depict the neurotransmitter levels associated with a particular event. FIG. 7 illustrates other exemplary graphical user interface configured to display neurotransmitter levels associated with an activity acquired from a user's mobile device according to examples of the disclosure. In one example, a user can be shown graphical user interface 702 which can represent the neurotransmitter levels associated with a particular event as a bar graph as discussed above with respect to FIG. 5. In another example, a user can be provided with a graphical user interface 704 which can express the same information in a textual format. Graphic visualization can provide a further base for reflection and learning about the drivers behind the happiness created or not created during an event. For instance, high Cannabinoid values at work can illustrate that a user's job provides additional levers (friends) to the user's happiness than a "normal" job that can mainly provide Dopamine (money, challenge) and Serotonin (recognition). With this provided knowledge, the user can potentially draw the conclusion that the added cannabinoid for the job might be a good reason to keep the job despite higher paid job alternatives.

In one or more examples, the graphical user interfaces presented in the example of FIG. 7 can also be configured to show any gaps between the actual neurotransmitter levels calculated as discussed above, and the maximum potential neurotransmitter level that could have been achieved for a given event. For instance, in one or more examples, a user can click on an individual neurotransmitter shown in graphical user interface 702, and be presented with graphical user interface 704 which not only shows in textual format the level of that neurotransmitter but could also display what percentage of the maximum realizable level the user achieved.

A user will usually experience more than one event per day, so in addition to calculating neurotransmitter levels associated with a single event, in one or more examples, the application can also show the user their neurotransmitter levels over a given period of time (such as a day, week, month, year) to provide the user with a sense of how their neurotransmitter levels are varying over time. Furthermore, and as described in detail below, simply knowing the levels of neurotransmitters during a given time period may be inadequate to allow the user to know if they are achieving peak mental health (i.e., happiness) and therefore, in one or more examples, the neurotransmitter levels over a given period of time can be converted into a metric that is indicative of how adequately the user is engaging in activities that promote happiness. In one or more examples, this metric can be referred to as a Return on Happiness (ROH).

ROH can provide the user with a universal indicator for happiness that can be applicable to all human beings, and can allow for an individual to quantitatively compare their happiness levels over time, in varying conditions, and with others. In one or more examples, ROH can function like other biomarkers such as blood pressure, heart rate, etc, in the sense that the value can allow the user to understand if their happiness level is developing positively or negatively over time and why. In the examples provided herein, ROH is discussed in terms of neurotransmitter levels, but the example should not be seen as limited to neurotransmitter levels, and the system and methods herein could be applied to ROH calculations involving other types of information that are correlated with happiness.

Returning to the example of FIG. 1, once the application calculates individual neurotransmitter activity and gaps at step 110, the process 100 can move to step 112 wherein the application can calculate actual neuroscientific happiness level (i.e., ROH) and also display any gaps between actual ROH and potential ROH. In one or more examples, ROH can be a metric that quantifies short- and long-term happiness based on adding up all the neurotransmitter activities within a given period of time. The ROH metric can simply be calculated by adding up all neurotransmitter activities triggered within a given period of time. For instance, the ROH for a given day can be calculated by adding up all of the neurotransmitter levels for each event over a given day.

While the ROH calculation can help the user to visualize or understand their neurotransmitter levels over a given period of time, it may not provide the user with a sense of whether or not they are achieving optimal neurotransmitter levels associated with positive mental health (i.e., happiness). Thus, in one or more examples, it may be useful to calculate an optimal value of ROH that each user should strive for in a given period of time such that the user is able to perceive gaps and deficiencies in their neurotransmitter levels over a given period of time.

Figure 8A:
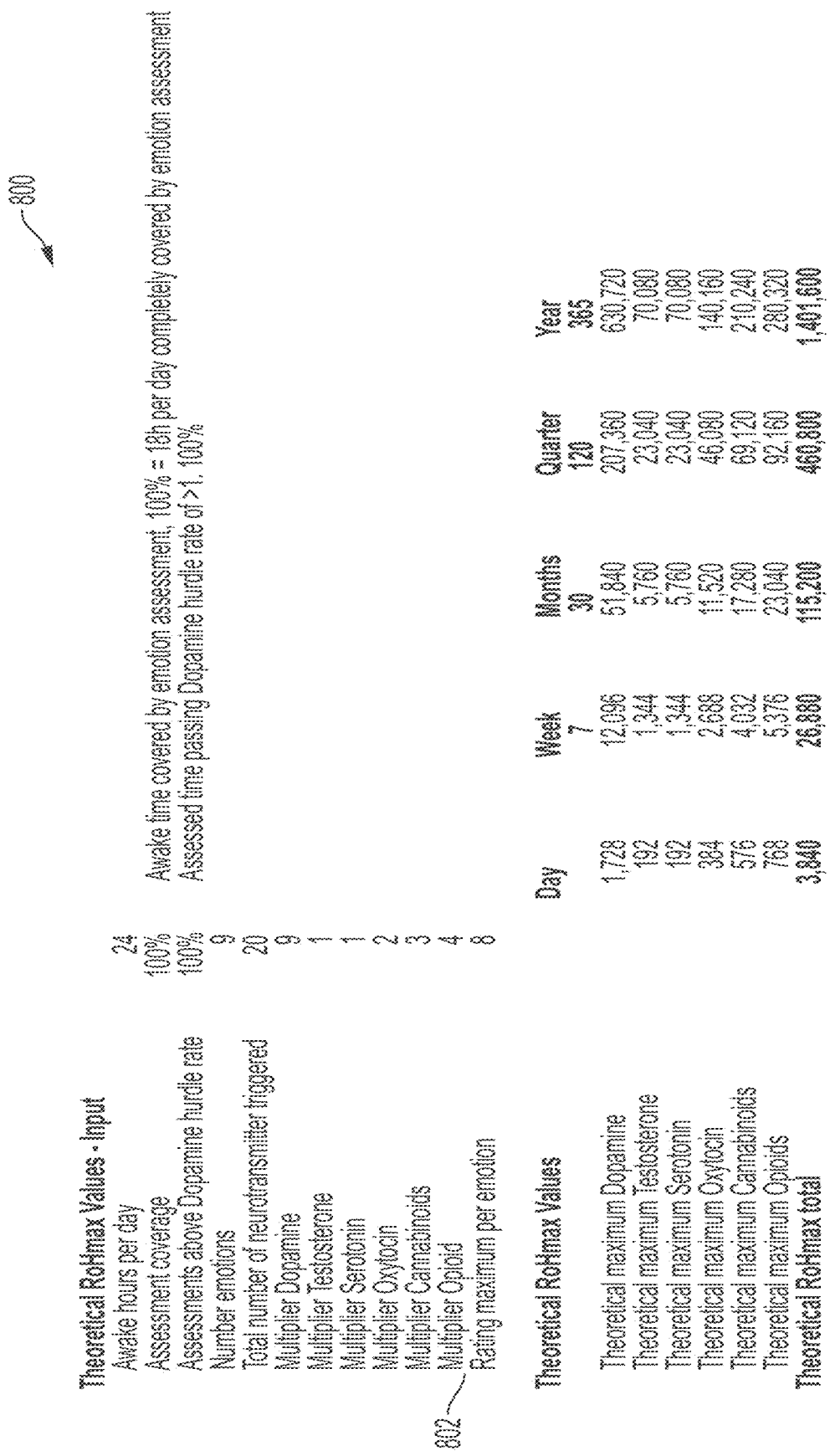
FIGS. 8A-8B illustrates an exemplary calculation for determining maximum neurotransmitter levels a brain can create at a given period of time according to examples of the disclosure.
Figure 8A:
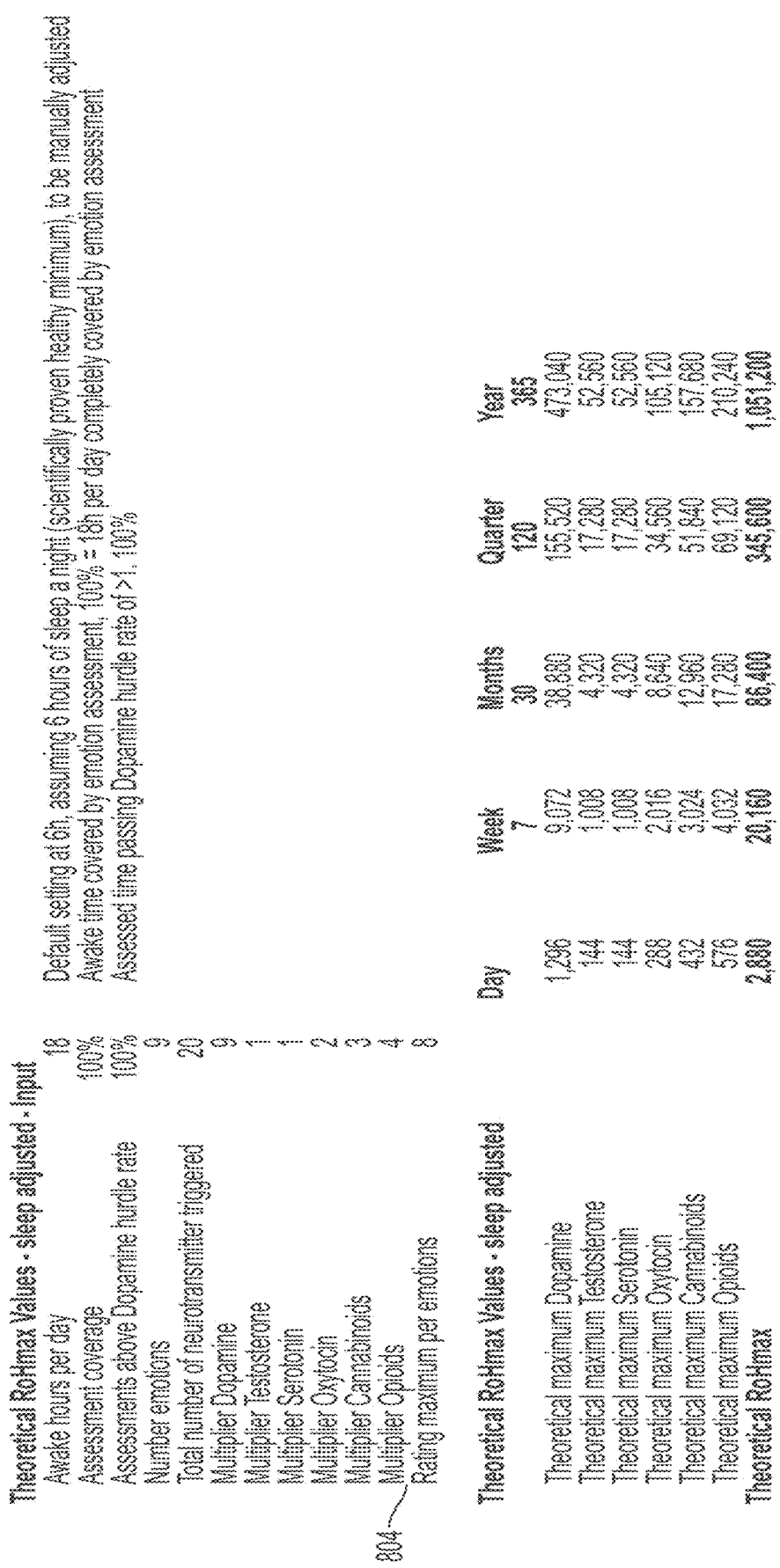
Figure 8B:
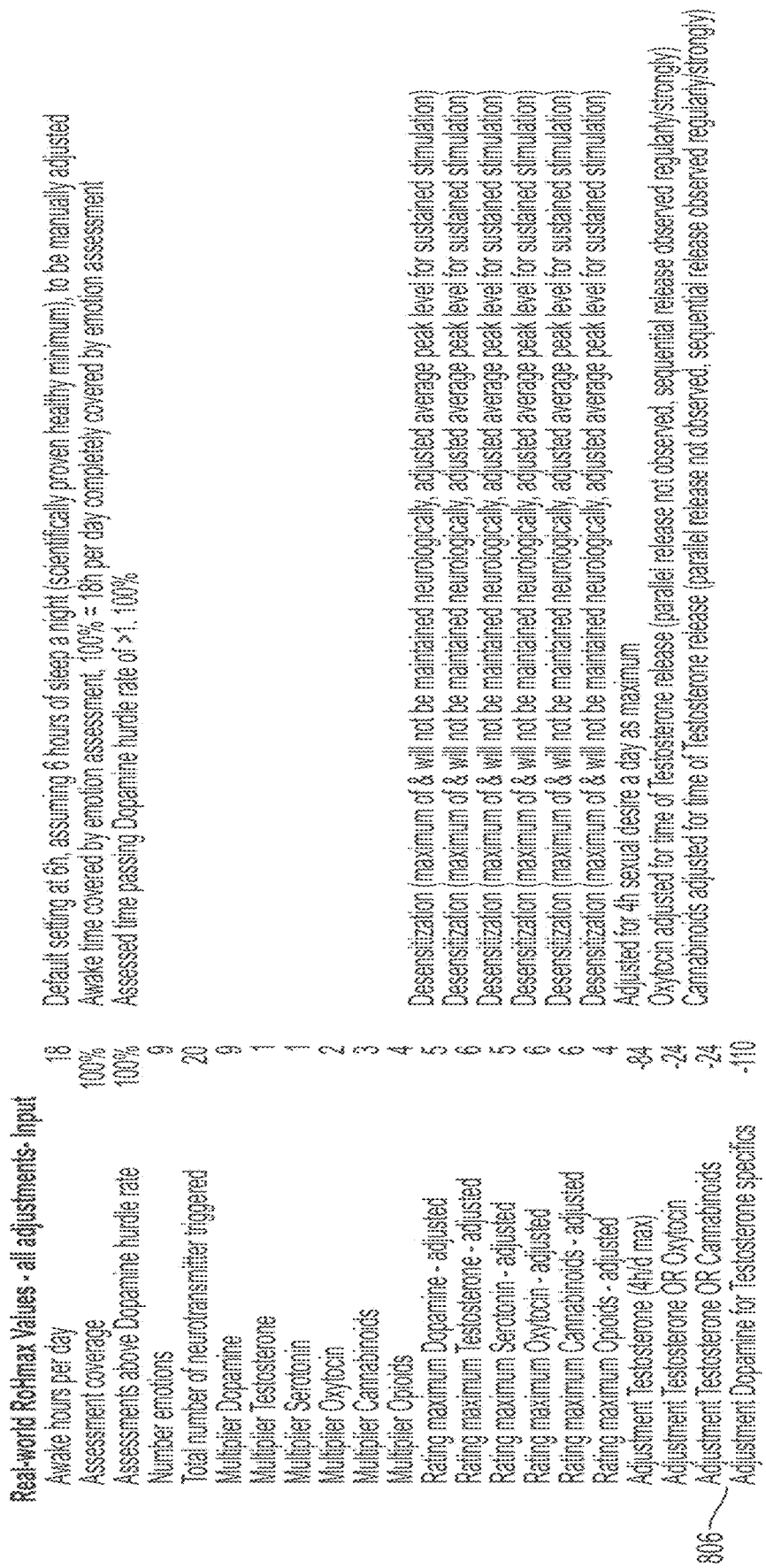

FIGS. 8A-8B illustrates an exemplary calculation for determining maximum neurotransmitter levels a brain can create at a given period of time according to examples of the disclosure. In one or more examples of the disclosure, the example calculation 800 of FIGS. 8A-8B can illustrate an theoretical maximum ROH calculation for a period of 24 hours. To calculate the theoretical max, the calculation can begin by assuming that a hypothetical individual is experiencing the maximum level of neurotransmitter release for all neurotransmitters over the full 24 hour period as shown at 802 of the calculation 800. As shown at 802, a theoretical maximum (assuming full release over 24 hours) can be calculated for each individual neurotransmitter as well as the overall ROH value. In one or more examples, and as shown at 802, the theoretical maximum for ROH and each neurotransmitter can be calculated over multiple periods of time (i.e., a day, a week, a month, a quarter, a year, etc.)

The calculation done at 802 may not be an accurate representation of the theoretical maximum values for ROH and each neurotransmitter, because human beings do not generally stay awake for 24 hours. Therefore, in one or more examples, the calculation can adjust the theoretical maximums calculated at 802 to account for periods of time when the individual is sleeping. In one or more examples, the calculation 800 can adjust the 24 hour theoretical maximum calculated at 802, to account for sleep as depicted at 804. In the example of 804, the total theoretical maximums can be adjusted to account for the user being asleep for approximately 6 hours in a given day. This adjustment can be employed for each of the ROH calculation periods (day, week, month, etc).

In one or more examples, simply adjusting for sleep, may not yield an accurate theoretical maximum, because the theoretical maximum may not account for certain "real world" realities regarding the generation of neurotransmitters. For instance, assuming a person is expressing maximum dopamine for the entire time that they are awake may not be realistic. In another example, it may not be realistic to assume that a person is expressing maximum testosterone for their entire waking day. Thus, in one or more examples of the disclosure, the adjusted calculation made at 804 can be further adjusted to account for "real world" realities as depicted in 806.

In addition to adjusting the maximum levels to account for the fact that individuals do not express maximum neurotransmitters for the entirety of their waking day, in one or more examples, the adjustment made at 806 can also account for the fact that certain neurotransmitters are mutually exclusive of one another. For instance, in one or more examples, oxytocin may not be released in parallel with testosterone, but rather they may be observed to be sequentially released. Thus, in one or more examples, the theoretical maximum calculation can be adjust at 806 to account for the reality that not all of the neurotransmitters may be present simultaneously.

In one or more examples of the disclosure, once the "real-world" adjustments are made at step 806, the resulting theoretical maximums for ROH and each neurotransmitter can be used as the final calculation of the theoretical maximums by which the actual levels calculated above are compared against.

Figure 9:
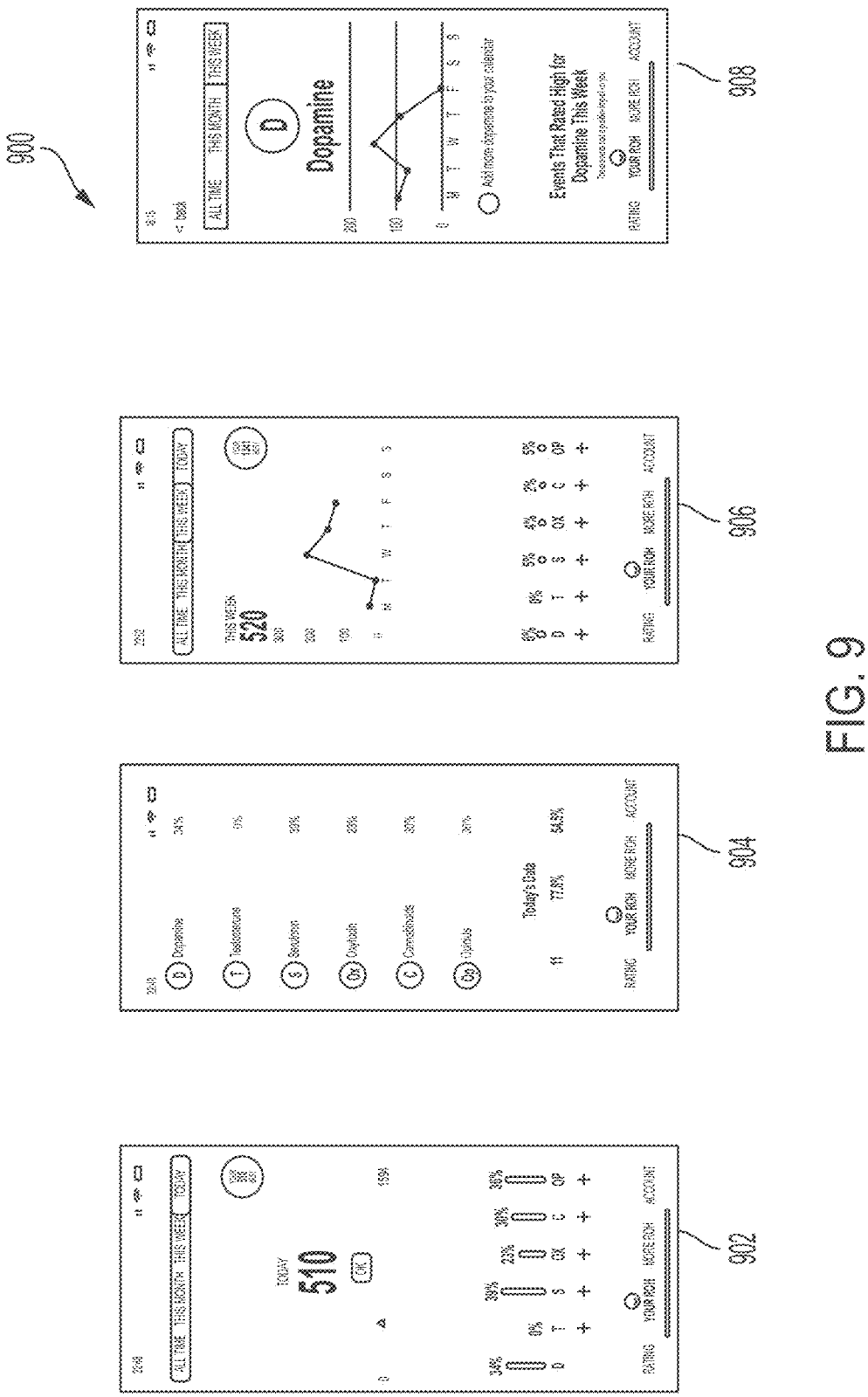
FIG. 9 illustrates exemplary graphical user interface configured to display ROH calculations acquired from a user's mobile device and show gaps between actual levels and desired levels according to examples of the disclosure.

Returning to the example of FIG. 1, once the application calculates actual neuroscientific happiness level and potential at step 112, the process 100 can move to step 114 wherein the user is provided with one or more graphical user interfaces or other visual cues configured to allow for the user to perceive gaps and potential to achieve better mental health. Thus at step 114, the user can be presented with one or more graphical user interfaces that are configured to allowed the user to gauge any gaps or deficiencies in their calculated ROH for a given period of time FIG. 9 illustrates exemplary graphical user interface configured to display ROH calculations acquired from a user's mobile device and show gaps between actual levels and desired levels according to examples of the disclosure. In one or more examples, the graphical user interfaces 900 can include a first graphical user interface 902 in which a user can view their individual ROH quantity for a given time period and its development. In one or more examples, the user at graphical user interface 902 can select a certain time period (i.e., day, week, month, etc) and be shown a "gas tank" chart which shows their actual ROH for the selected time period as well as the "gap" between their actual ROH and the calculated theoretical optimal or maximum ROH.

In one or more examples, and alternatively to the example of graphical user interface 902, the user can be presented with graphical user interface 904 which can show a line graph of their ROH level over a given period of time. For instance, in the example of graphical user interface 904, the user can be presented with a line graph which plots the ROH levels for each day of a given week, and can indicate the average daily ROH they achieved over the week.

In one or more examples, the graphical user interfaces 900 can include a third graphical user interface 906 which can be configured to provide the user with a view of neurotransmitter patterns and percentages based on the calculations discussed above with respect to FIGS. 6 and 7.

In one or more examples, the graphical user interfaces 900 can include a fourth graphical user interface 908 which can be configured to show the user the variations in a particular neurotransmitter level over a given period of time. For instance, in the particular example of graphical user interface 908, the user can be shown their dopamine levels over a given week by using a line graph that plots dopamine levels for each day of the week during the given week.

In addition to identifying gaps and deficiencies in ROH as well as gaps and deficiencies in individual neurotransmitter levels, in one or more examples, the application can be configured to offer the user one or more suggestions for obtaining their peak or optimal ROH levels as well as their peak or optimal individual neurotransmitter levels. In doing so, the application can not only diagnose deficiencies in ROH and neurotransmitter levels, but it can also provide the user with goals and activities designed to improve those levels thereby helping the user of the application achieve optimal or peak mental health. Thus, returning to the example of FIG. 1, in one or more examples, after the process 100 apprises the user of any gaps and/or potential opportunities for better mental health, the process can move to step 116 wherein the application can suggest personalized improvements from one or more event databases (as described in further detail below.)

Figure 10:
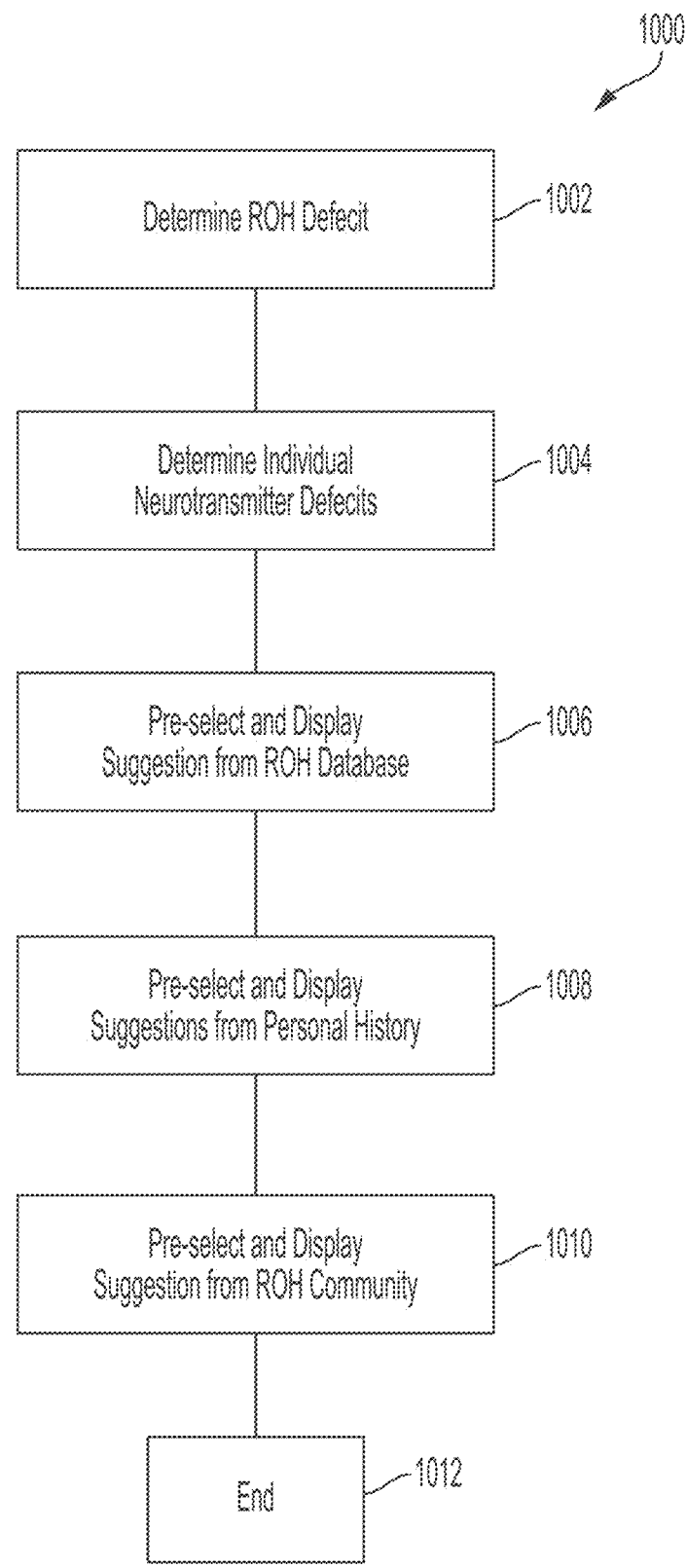
FIG. 10 illustrates an exemplary process for providing suggestions to improve ROH and individual neurotransmitter levels according to examples of the disclosure.

FIG. 10 illustrates an exemplary process for providing suggestions to improve ROH and individual neurotransmitter levels according to examples of the disclosure. In one or more examples, the process 1000 of FIG. 10 can begin at step 1002 wherein the application can determine an ROH deficit as described above with respect to FIGS. 8 and 9 above. Once the application has determined a particular ROH deficit at step 1002, the process 1000 can move to step 1004 wherein deficits for individual neurotransmitters are calculated according to the examples provided above.

In one or more examples, after the process 1000 calculates the ROH deficits and neurotransmitter deficits at steps 1002 and 1004 respectively, the process 1000 can move to step 1006, wherein the application can pre-select and display a suggestions from a database that contains activities which are configured to increase overall ROH (explained in further detail below). In one or more examples of the disclosure, the pre-selection of suggestions made at step 1006 can be based on individual ROH level calculated as described above. For instance, if the user exhibits ROH from 0 to a predetermined threshold, and is found to have low activity based on the data downloaded from the application, the then at step 1006 the application can randomly select one or more ROH activities from the database that are associated with "understimulation." If the ROH levels are low, but the activity determination is high, then in one or more examples the application can randomly select one or more ROH activities that are associating with "overstimulation."

In one or more examples, if the ROH value is determined to be above the predetermined threshold, but is still below a second predetermined threshold, then the application can select one or more activities from the that database that are associated with "Optimum" values. In one or more examples, if the ROH value is determined to be above the second predetermined threshold, then in one or more examples, the application can randomly select one or more ROH activities from the database that are associated with a "peak" section of the database.

In one or more examples, and at step 1006, entries from the ROH database can be selected to address individual neurotransmitter deficiencies as well. As discussed in further below, the ROH database can not only be categorized based on "understimulation," "overstimulation," "optimal," and "peak," but can also be categorized with respect to individual neurotransmitters.

Figure 11A:
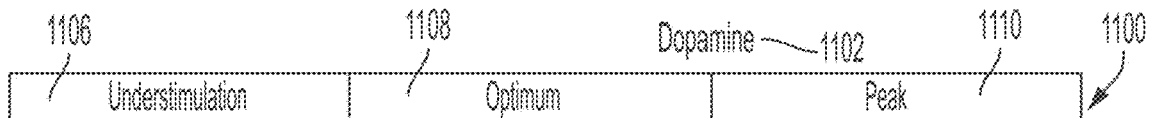

FIGS. 11A-C illustrate an exemplary database of suggestions for activities based on ROH and individual neurotransmitter levels according to examples of the disclosure. In the example of FIGS. 11A-C, the database 1100 can be specifically configured to provide suggestion relating to increasing dopamine and testosterone levels as indicated at 1102 and 1104. The activities listed under the dopamine section 1102 of the database 1100 can include activities meant to promote increased or optimal dopamine levels in the body. Likewise, the testosterone section 1104 can be configured to include activities meant to promote increased or optimal testosterone levels in the body.

In one or more examples, and as described above, under each neurotransmitter, the database 1100 can include suggestions pertaining to understimulation (1106), optimum (1108), peak (1110), and overstimulation ROHs as described in detail above. Thus, when the application selects an activity to suggest, the application can retrieve a suggestion pertaining to the individual neurotransmitter as well as the level of ROH that the user is determined to presently have. In the case of suggestions for improving overall ROH, the application can randomly choose a particular suggestion pertaining to a randomly chosen neurotransmitter and a determined level of ROH to suggest to the user.

Figure 12A:

FIGS. 12A-C illustrates another exemplary database of suggestions for activities based on ROH and individual neurotransmitter levels according to examples of the disclosure. The example of FIG. 12 can be similar to the example of FIGS. 11A-C except that the database 1200 is configured to provide suggestions for optimizing serotonin (as indicated at 1202) and oxytocin (as indicated at 1204). In one or more examples, the suggestions provided at steps 1006 can be selected from the database 1200 similar to the procedure described above with respect to FIG. 11.

FIGS. 13A-B illustrates an exemplary database of suggestions for activities based on ROH and individual neurotransmitter levels according to examples of the disclosure. The examples of FIG. 13A-B can be similar to the example of FIG. 11A-C except that the database 1300 is configured to provide suggestions for optimizing cannabinoids (as indicated at 1302) and opioids (as indicated at 1304). In one or more examples, the suggestions provided at steps 1006 can be selected from the database 1300 similar to the procedure described above with respect to FIG. 11A-C.

Returning to the example of FIG. 10, in one or more examples, after pre-selecting and displaying selections from the ROH database at step 1006, the process 1000 can move to step 1008 wherein the application can pre-select suggestions based on the user's personal event history. In one or more examples, past user events can be filter for ROH values that are above a predetermined threshold. The predetermined threshold can be a value that is indicative of an event that engendered strong positive emotions. If a user is seeking to increase their ROH, then the application can suggest past activities that were filtered for producing ROH greater than the predetermined threshold.

In one or more examples, after suggesting past user events to the user that were associated with increased ROH at step 1008, the process 1000 can move to step 1010 wherein the application can pre-select a display suggestions from a "ROH community." In one or more examples, suggestions from the "ROH community" can include suggesting activities that caused other users to experience increased ROH who also were using the same application on their computing devices. In order to obtain these suggestions, in one or more examples the application can be connected to the internet or other computing network and share data with a server or other computing devices so that they can utilize each other's activity data to find suggestions for increasing ROH. Once the user has been provided with ROH community suggestions at step 1010, the process 1000 can move to step 1012 wherein the process is terminated.

Figure 14:
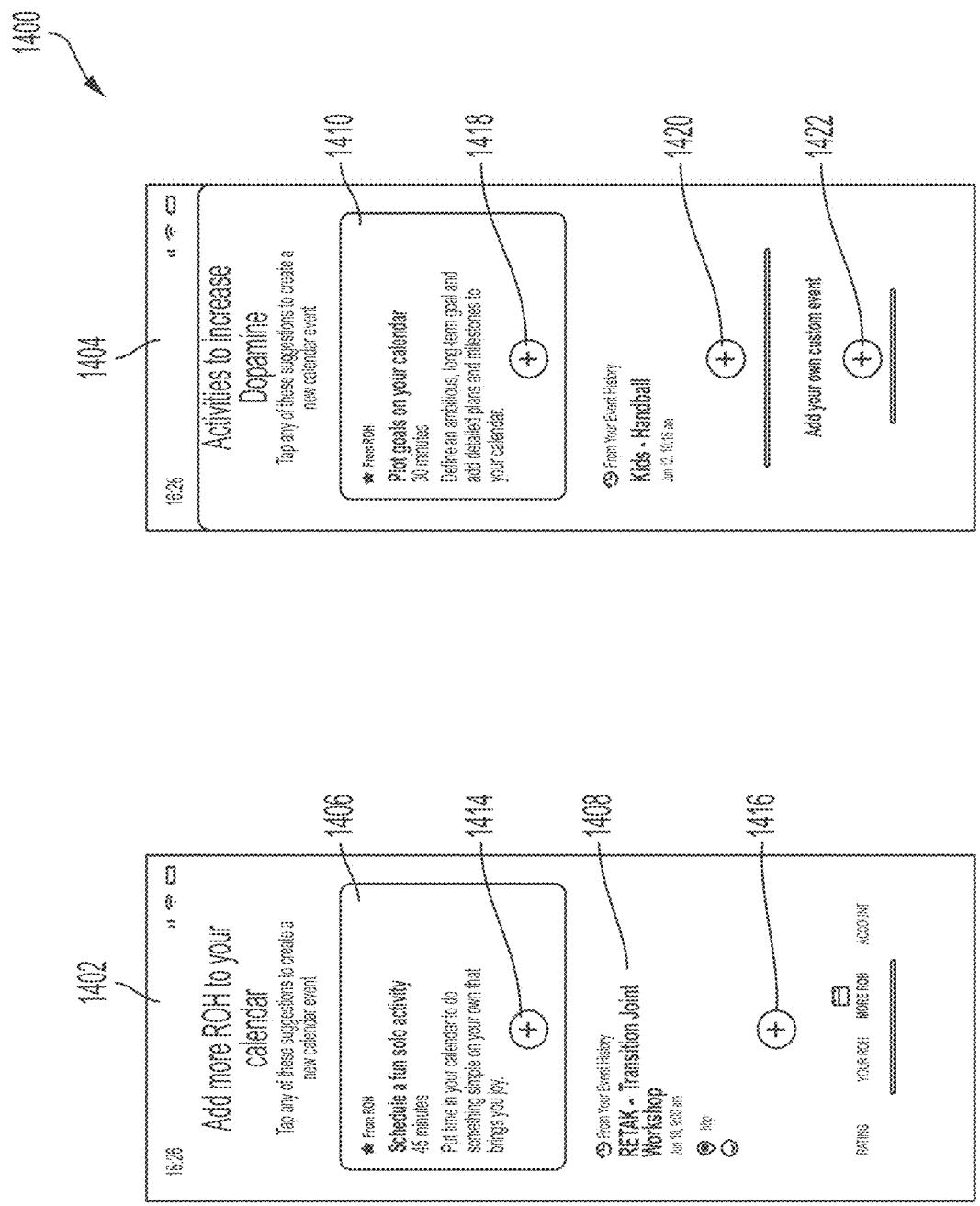
FIG. 14 illustrates an exemplary graphical user interface configured to provide the user with suggestions of activities for increasing neurotransmitter levels associated with positive mental health according to examples of the disclosure.

FIG. 14 illustrates an exemplary graphical user interface configured to provide the user with suggestions of activities for increasing neurotransmitter levels associated with positive mental health according to examples of the disclosure. In one or more examples, the graphical user interfaces 1400 can be configured to display the suggestions provided by the process 1000 of FIG. 10 to the user. In one or more examples, the graphical user interfaces can include a first graphical user interface 1402 which provide one or more suggestions to the user to increase their overall ROH score. In one or more examples the graphical user interface 1402 can include a panel 1406 that can suggest an activity from the ROH database (described above with respect to FIGS. 10-13). The panel 1406 can include a user selectable button 1414 that if selected by the user, can prompt the user to create a calendar event based on the suggested activity (described in further detail below). In one or more examples, rather than prompting the user to create a calendar event, the user can simply be prompted via a notification to plan for more events that will promote happiness. For instance, the user can be prompted in the early evening to plan for more happiness events for the next day, or can be prompted on a Sunday evening to plan for more happiness events during the week to promote overall biological happiness.

In one or more examples, the graphical user interface 1402 can include a panel 1408 that can suggest an activity from the personal history of the user (described above with respect to FIG. 10). The panel 1408 can include a user selectable button 1416 that if selected by the user, can prompt the user to create a calendar event based on the suggested activity (described in further detail below).

The graphical user interface 1402 can be used to suggest specific activities to improve overall ROH. In one or more examples, and as described above, a graphical user interface could also be deployed to the user to provide suggestions for increasing levels of a specific neurotransmitter. Thus, in one or more examples, the graphical user interfaces 1400 can include a graphical user interface 1404 configured to provide suggestions to the user to increase a specific neurotransmitter. In the example of graphical user interface 1404, the user can be provided suggestions to increase their level of dopamine. In one or more examples the graphical user interface 1404 can include a panel 1410 that can suggest an activity from the ROH database (described above with respect to FIGS. 10-13). The panel 1410 can include a user selectable button 1418 that if selected by the user, can prompt the user to create a calendar event based on the suggested activity that is configured to increase dopamine levels of the user (described in further detail below).

In one or more examples, the graphical user interface 1404 can include a panel 1412 that can suggest an activity from the personal history of the user (described above with respect to FIG. 10). The panel 1412 can include a user selectable button 1420 that if selected by the user, can prompt the user to create a calendar event based on the suggested activity (described in further detail below). In one or more examples, the graphical user interface 1404 can include a user selectable button 1422 that when selected by the user can allow the user to create their own custom event rather than using a suggestion provided by the application.

Returning to the example of FIG. 1, once the application provides the user with suggestions per the discussion above with respect to FIGS. 10-14, the process can move to step 118 wherein the user can decide and activate personalized improvement suggestions. In one or more examples, the user can decide and activate personalized improvement suggestions by selecting one of the user selectable buttons 1414, 1416, 1418 or 1420 described above with respect to FIG. 14. Once the user has selected and active one or more personalized suggestions at step 118, the process 100 can move to step 120, wherein the user adds the suggestions to their digital calendar stored on their mobile computing device.

Figure 15:
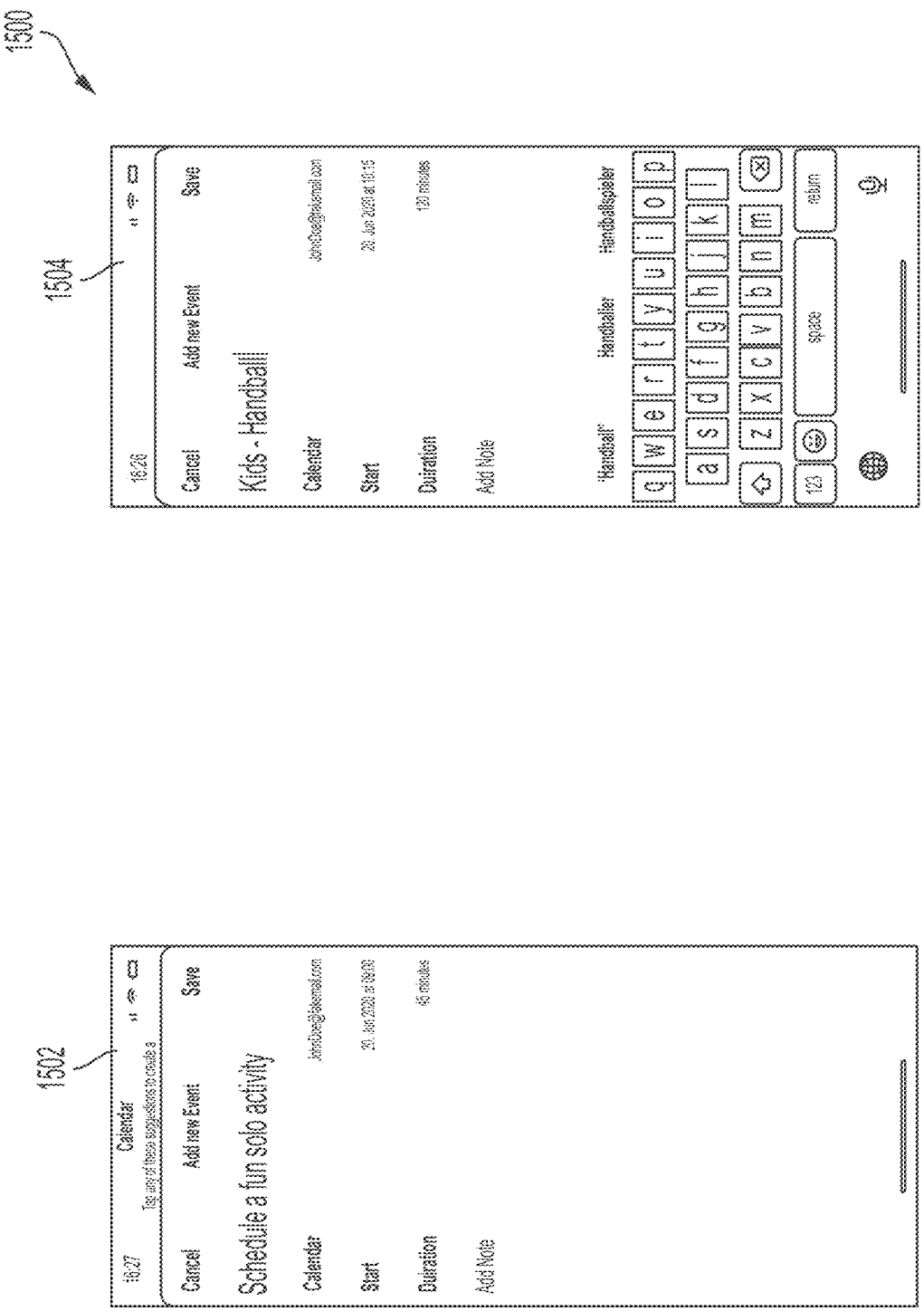
FIG. 15 illustrates graphical user interfaces configured to allow a user to add suggestions to their digital calendar according to examples of the disclosure.

At step 120, when the user adds a personalized suggestion at step 120, they can be presented with one or more graphical user interfaces that can be configured to add an event to their calendar. FIG. 15 illustrates graphical user interfaces configured to allow a user to add suggestions to their digital calendar according to examples of the disclosure. In the example of FIG. 15, the graphical user interfaces 1500 can include a first graphical user interface 1502 that allows the user to add a suggested event from the ROH database. Returning to the example of FIG. 14, if the graphical user interface 1402 suggests scheduling a fun solo activity at panel 1406, if the user selects button 1414 to add the event, then they can be direct to graphical user interface 1502 to add the event to their calendar. The graphical user interfaces 1500 can include a second graphical user interface 1504 that allows the user to add a suggested event from their personal history. Returning to the example of FIG. 14, if the graphical user interface 1404 suggests scheduling a kids handball event (based on past history), if the user selects button 1420 to add the event, then they can be direct to graphical user interface 1504 to add the event to their calendar.

The example process of FIG. 1, as described above, can ensure that that the user experiences positive behavior change that is specific to happiness and/or neurotransmitter gaps and potential. The provided suggestions can be configured to ensure that the suggested presented are ambitious but achievable. This can drive motivation to add the suggestion to the calendar in a near term time frame and thus makes it more likely that the user will act on the suggestion In one or more examples, the suggestion can be filtered such that they are configured to make it more likely that they trigger a ROH rating higher than the current average ROH of the user when executed. Taking the active responsibility for the decision to change future behavior can trigger perceived personal ownership for your own happiness. The suggestions thus can be designed to provide a near-term read-out with a high likelihood for positive emotions with high positive reinforcement potential triggered. The example process 100 of FIG. 1 can thus be configured to initiate and maintain a positive reinforcement loop that can continuously drive ROH improvements week-over-week thereby improving the mental health of the user of the application.

Figure 16:
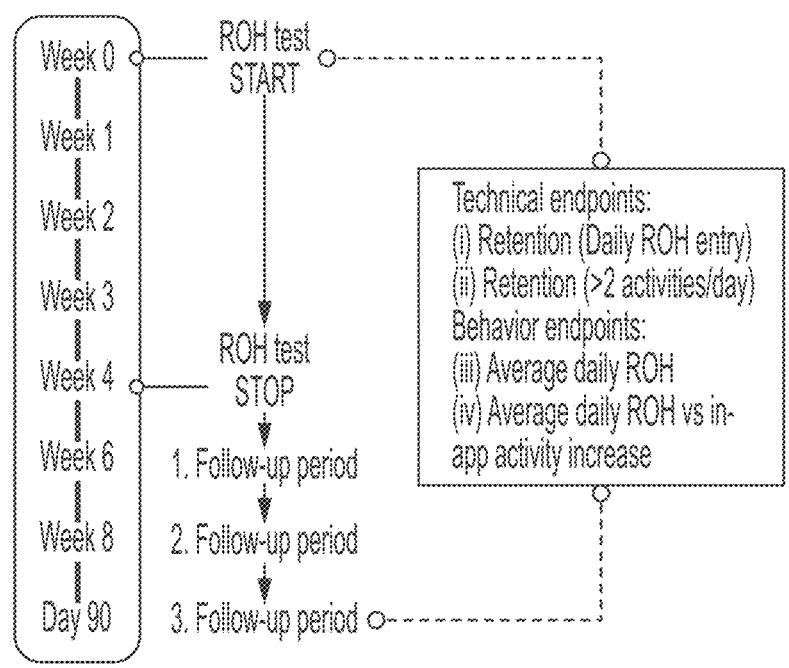
FIG. 16 illustrates a test design previously conducted to determine the level of user engagement with the system described above as well as the system's impact on overall ROH of a user according to examples of the disclosure.

During field testing, the systems and methods described above have delivered unexpected results showing that using techniques for gathering and delivering to and from a user regarding their ROH, has not only led to an overall increase in a user's ROH over time, but has also effectively kept user's engaged with the program over a significantly long duration of time. FIG. 16 illustrates a test design previously conducted to determine the level of user engagement with the system described above as well as the system's impact on overall ROH of a user. The ROH test design comprised a four week period with continuous/daily data assessment, and upon completion of the initial four week period, three follow-ups were conducted at six weeks, eight weeks and ninety days after a user began the program outlined by the systems and methods described above. During the tests, multiple data points were taken. User retention was checked to see if the user was entering daily activities using the application, as well as determining if the user was entering at least two or more activities on average per day using the application. During testing, the user's average daily ROH results were recorded, and any correlation between average daily ROH development and increase use of the application were determined.

FIG. 17 illustrates the attrition and number of participants/users during the ROH test over time and the retention rates. Retention was calculated for the test period of four weeks (line J) and the three follow-up periods of 42 days (line K), 56 days (line L), and 90 days (line M), respectively. User retention was determined by available daily ROH recordings for each user measured at the end of the test period (Columns 4, 6, and 8) and by uses with more than 2 in-app activities per day per user (Column 5, 7, and 9). In addition, retention was calculated versus users who started rating (Columns 4 and 5), vs users who installed the ROH app (Columns 6 and 7), and versus users who were selected and randomized (Columns 8 and 9). The results of the test shows that 52% of users were retained over a 28 day period, 33% continued to use the application after 42 days, 24% users continued to use the application after 56 days, and 24% of users continued to use the application after 90 days. Thus, the format of the application, including the graphical user interfaces designed to engage a user unexpectedly caused approximately ¼ of all users to continue using the application even at 90 days after the initial test was started. The results also showed that a significant percentage of users not only were using the application over time, but were also performing two or more activities on the application per day. As shown in the test data of FIG. 17, 38% of the users were active in the application more than 2 times on a daily basis after 28 days, 29% of users were active in the application more than 2 times on a daily basis after 42 days, and 16% of the users were active in the application more than 2 times on a daily basis after 56 days.

Figure 18:
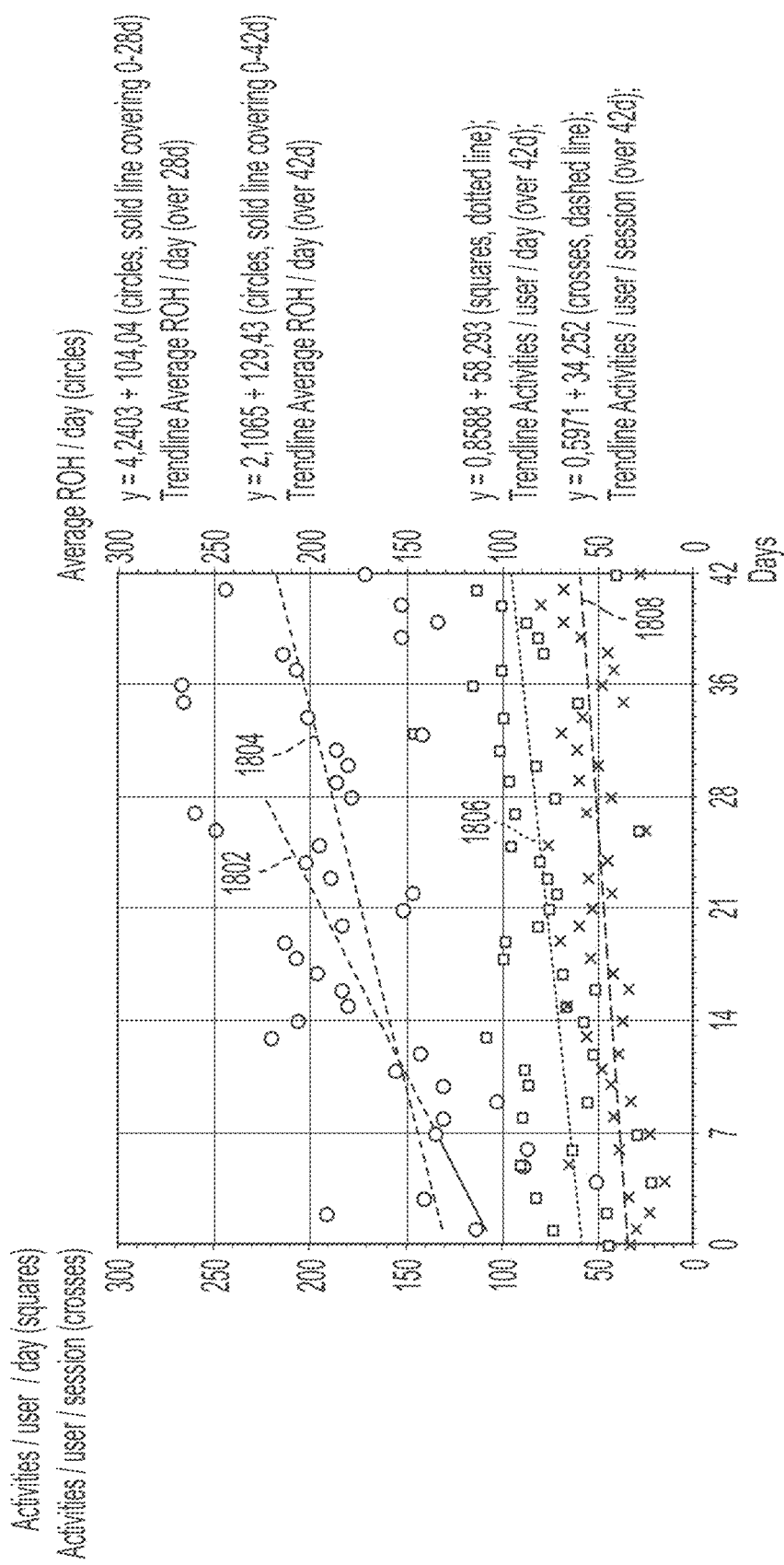
FIG. 18 illustrates test data showing how ROH improved over time for various categories of users according to examples of the disclosure.

In addition to retaining users, the systems and methods described above also improved average daily ROH values over time as user continued to use the application. FIG. 18 illustrates test data showing how ROH improved over time for various categories of users. The black circle in the graph, show average daily ROH values for users over time, daily activities per user (squares) and daily activities per session per user (crosses) over time. In addition, four linear trend lines including formulas have been calculated on the test data as shown in FIG. 18. Trend line 1802 illustrates average ROH of a user per day covering a 28-day period (solid line covering the range from d0 to d28). Trend line 1804 shows average ROH of a user per day covering a 42-day period (solid line covering the range from d0 to d42). Trend line 1806 illustrates the number of activities per user per day covering a 42-day period (dotted line). Finally, trend line 1808 shows activities per user per session covering a 42-day period (dashed line). Overall the data shows that over a 42-day period, daily ROH representing positive emotion ratings increased 2-3.5× as fast as the increase in application utilization, which strongly suggests an improvement of emotional significance during rated events experienced in the test period. The daily ROH increase was shown to be particularly strong (>4.5×) in the first four weeks as indicated by trend line 1802.

Figure 19:
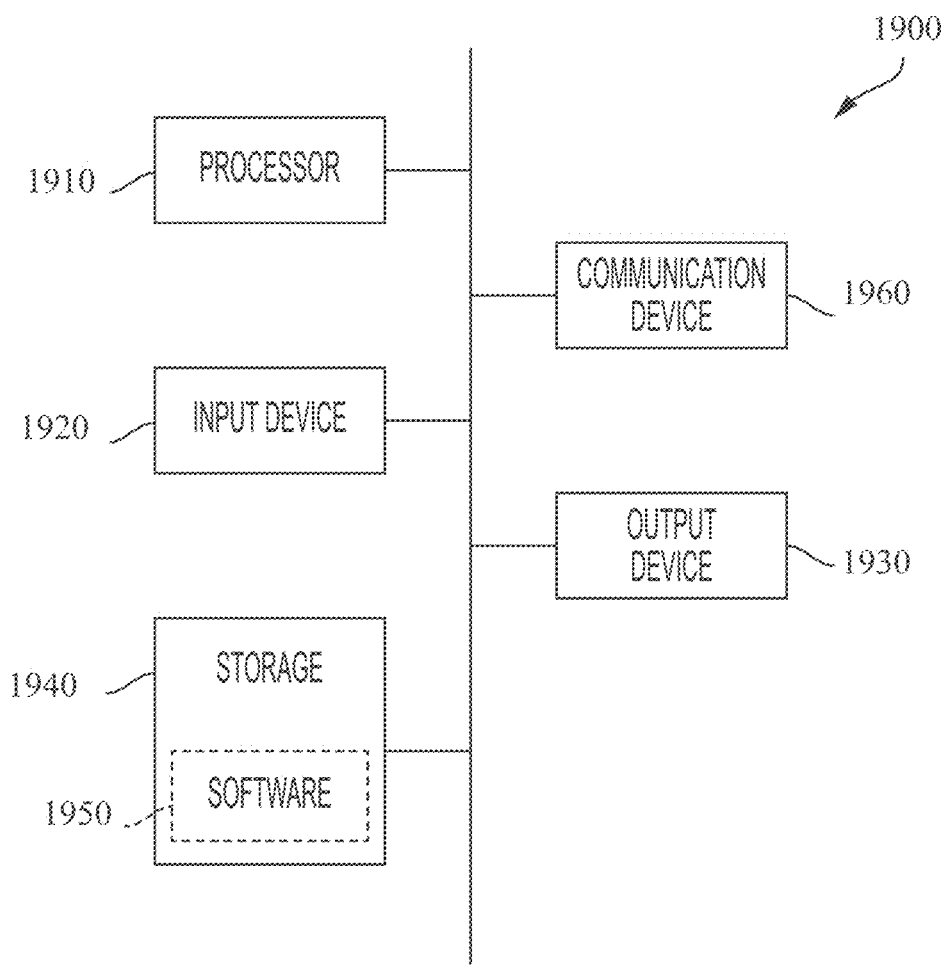
FIG. 19 illustrates an example of a computing device in accordance with one embodiment.

FIG. 19 illustrates an example of a computing device in accordance with one embodiment. Device 1900 can be a host computer connected to a network. Device 1900 can be a client computer or a server. As shown in FIG. 19, device 1900 can be any suitable type of microprocessor-based device, such as a personal computer, workstation, server, or handheld computing device (portable electronic device) such as a phone or tablet. The device can include, for example, one or more of processor 1910, input device 1920, output device 1930, storage 1940, and communication device 1960. Input device 1920 and output device 1930 can generally correspond to those described above and can either be connectable or integrated with the computer.

Input device 1920 can be any suitable device that provides input, such as a touch screen, keyboard or keypad, mouse, or voice-recognition device. Output device 1930 can be any suitable device that provides output, such as a touch screen, haptics device, or speaker.

Storage 1940 can be any suitable device that provides storage, such as an electrical, magnetic, or optical memory, including a RAM, cache, hard drive, or removable storage disk. Communication device 1960 can include any suitable device capable of transmitting and receiving signals over a network, such as a network interface chip or device. The components of the computer can be connected in any suitable manner, such as via a physical bus or wirelessly.

Software 1950, which can be stored in storage 1940 and executed by processor 1910, can include, for example, the programming that embodies the functionality of the present disclosure (e.g., as embodied in the devices as described above).

Software 1950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1940, that can contain or store programming for use by or in connection with an instruction execution system, apparatus, or device.

Software 1950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Device 1900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1900 can implement any operating system suitable for operating on the network. Software 1950 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

This application discloses several numerical ranges in the text and figures. The numerical ranges disclosed inherently support any range or value within the disclosed numerical ranges, including the endpoints, even though a precise range limitation is not stated verbatim in the specification, because this disclosure can be practiced throughout the disclosed numerical ranges.

The above description is presented to enable a person skilled in the art to make and use the disclosure, and it is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown but is to be accorded the widest scope consistent with the principles and features disclosed herein. Finally, the entire disclosure of the patents and publications referred in this application are hereby incorporated herein by reference.

What is claimed is:

1. A method for assessing neurotransmitter levels of a user based on a user's activity data stored on a computing device, the method comprising:

receiving data from a computing device associated with the user, wherein the received data is associated with one or more activities performed by the user;

displaying a first graphical user interface at the display, wherein the first graphical user interface is configured to display and receive one or more categorizations of the one or more activities performed by the user from the user;

determining one or more emotions based on the received one or more categorizations of the one or more activities performed by the user;

displaying a second graphical user interface at the display, wherein the second graphical user interface is configured to receive one or more quantitative ratings corresponding to each of the determined one or more emotions from the user;

determining one or more neurotransmitter activity levels of the user by applying the received one or more quantitative ratings received from the user to a positive emotion to neurotransmitter (PE-NT) matrix, wherein the PE-NT matrix indicates respective correspondences between a plurality of positive emotions and a plurality of neurotransmitters associated with one or more of the emotions of the plurality of positive emotions, such that, for each emotion of the determined one or more emotions from the user, the PE-NT matrix indicates one or more values, each value of the one or more values corresponding to a neurotransmitter of the plurality of neurotransmitters that is associated with the emotion, and wherein applying the received one or more quantitative ratings received from the user to the PE-NT matrix comprises multiplying one or more of the one or more values by a quantitative rating of the one or more quantitative ratings received from the user for the emotion;

determining one or more optimal neurotransmitter activity levels for the user;

determining one or more neurotransmitter deficiencies of the user, based on the determined one or more neurotransmitter activity levels of the user and the determined one or more optimal neurotransmitter activity levels for the user; and generating and displaying one or more suggestions for increasing the determined one or more neurotransmitter activity levels.

2. The method of claim 1, wherein the method comprises: displaying a third graphical user interface at the display, wherein the third graphical user interface is configured to display the determined one or more optimal neurotransmitter activities and the determined one or more neurotransmitter deficiencies.

3. The method of claim 2, wherein the third graphical user interface includes one or more user selectable features that when selected by the user allows the user to add an event corresponding to the one or more generated suggestions to an electronic calendar associated with the user.

4. The method of claim 1, wherein the generated one or more suggestions for increasing the determined one or more neurotransmitter are generated by selecting one or more entries from a database containing a plurality of suggestions for increasing neurotransmitter levels.

5. The method of claim 4, wherein the database containing a plurality of suggestions for increasing neurotransmitter levels is categorized based on one or more types of neurotransmitters.

6. The method of claim 4, wherein the database containing a plurality of suggestions for increasing neurotransmitter levels is categorized based on an amount of increase in the neurotransmitter levels needed.

7. The method of claim 1, wherein the categorizations received from the user comprises at least one category selected from the group consisting of: work and school, consumption, leisure, social, community service, religious, and spiritual.

8. The method of claim 1, wherein the determined one or more emotions comprises at least one emotion selected from the group consisting of: enthusiasm, sexual desire, pride, nurturant love, contentment, amusement, attachment love, pleasure, and gratitude.

9. The method of claim 1, wherein the second graphical user interface is configured to receive one or more lengths of time of the one or more activities performed by the user and determining the one or more neurotransmitter activity levels of the user includes applying the received one or more lengths of time of the one or more activities to the PE-NT matrix.

10. The method of claim 1, wherein the one or more neurotransmitter activity levels include one or more levels associated with: dopamine, testosterone, serotonin, oxytocin, cannabinoids, and opioids.

11. The method of claim 1, wherein determining the one or more emotions based on the received one or more categorizations of the one or more activities performed by the user is based on a behavior-to-positive emotion (B-PE) matrix.

12. The method of claim 1, wherein the method comprises determining an overall return on happiness (ROH) score based on the determined one or more neurotransmitter activity levels.

13. The method of claim 12, wherein the method comprises determining an optimal ROH score for the user.

14. The method of claim 13, wherein the method comprises determining one or more ROH score deficiencies of the user, based on the determined ROH score and the determined optimal ROH score for the user.

15. The method of claim 1, wherein determining the one or more neurotransmitter activity levels comprises, for each neurotransmitter of the plurality of neurotransmitters, summing the multiplied one or more values in the PE-NT matrix that correspond to the neurotransmitter.

16. The method of claim 15, wherein determining the one or more neurotransmitter activity levels comprises, for each neurotransmitter of the plurality of neurotransmitters, multiplying the summed value from the PE-NT matrix by a duration of the one or more activities of the user to determine the neurotransmitter activity level for the neurotransmitter.

17. A system for assessing neurotransmitter levels of a user based on a user's activity data stored on a computing device, the system comprising:
 a memory;
 a display;
 one or more processors; and
 one or more programs, wherein the one or more programs are stored in the memory and configured to be executed by the one or more processors, the one or more programs when executed by the one or processors cause the processor to:
  receive data from a computing device associated with the user, wherein the received data is associated with one or more activities performed by the user;
  display a first graphical user interface at the display, wherein the first graphical user interface is configured to display and receive one or more categorizations of the one or more activities performed by the user;
  determine one or more emotions based on the received one or more categorizations of the one or more activities performed by the user;
  display a second graphical user interface at the display, wherein the second graphical user interface is configured to receive one or more quantitative ratings corresponding to each of the determined one or more emotions from the user;
  determine one or more neurotransmitter activity levels of the user by applying the received one or more quantitative ratings received from the user to a positive emotion to neurotransmitter (PE-NT) matrix,
  wherein the PE-NT matrix indicates respective correspondences between a plurality of positive emotions and a plurality of neurotransmitters associated with one or more of the emotions of the plurality of positive emotions, such that, for each emotion of the determined one or more emotions from the user, the PE-NT matrix indicates one or more values, each value of the one or more values corresponding to a neurotransmitter of the plurality of neurotransmitters that is associated with the emotion, and
  wherein applying the received one or more quantitative ratings received from the user to the PE-NT matrix comprises multiplying one or more of the one or more values by a quantitative rating of the one or more quantitative ratings received from the user for the emotion;
  determine one or more optimal neurotransmitter activity levels for the user;
  determine one or more neurotransmitter deficiencies of the user, based on the determined one or more neurotransmitter activity levels of the user and the determined one or more optimal neurotransmitter activity levels for the user; and
  generate and display one or more suggestions for increasing the determined one or more neurotransmitter activity levels.

18. The system of claim 17, wherein the processor is further caused to:
 display a third graphical user interface at the display, wherein the third graphical user interface is configured to display the determined one or more optimal neurotransmitter activities and the determined one or more neurotransmitter deficiencies.

19. The system of claim 18, wherein the third graphical user interface includes one or more user selectable features that when selected by the user allows the user to add an event corresponding to the one or more generated suggestions to an electronic calendar associated with the user.

20. The system of claim 17, wherein the generated one or more suggestions for increasing the determined one or more neurotransmitter are generated by selecting one or more entries from a database containing a plurality of suggestions for increasing neurotransmitter levels.

21. The system of claim 20, wherein the database containing a plurality of suggestions for increasing neurotransmitter levels is categorized based on one or more types of neurotransmitters.

22. The system of claim 20, wherein the database containing a plurality of suggestions for increasing neurotransmitter levels is categorized based on an amount of increase in the neurotransmitter levels needed.

23. The system of claim 17, wherein the categorizations received from the user comprises at least one category selected from the group consisting of: work and school, consumption, leisure, social, community service, religious, and spiritual.

24. The system of claim 17, wherein the determined one or more emotions comprises at least one emotion selected from the group consisting of: enthusiasm, sexual desire, pride, nuturant love, contentment, amusement, attachment love, pleasure, and gratitude.

25. The system of claim 17, wherein the second graphical user interface is configured to receive one or more lengths of time of the one or more activities performed by the user and determining the one or more neurotransmitter activity levels of the user includes applying the received one or more lengths of time of the one or more activities to the PE-NT matrix.

26. The system of claim 17, wherein the one or more neurotransmitter activity levels include one or more levels associated with: dopamine, testosterone, serotonin, oxytocin, cannabinoids, and opioids.

27. The system of claim 17, wherein determining the one or more emotions based on the received one or more categorizations of the one or more activities performed by the user is based on a behavior-to-positive emotion (B-PE) matrix.

28. The system of claim 17, wherein the processor is further caused to determine an overall return on happiness (ROH) score based on the determined one or more neurotransmitter activity levels.

29. The system of claim 28, wherein the processor is further caused to determine an optimal ROH score for the user.

30. The system of claim 29, wherein the processor is further caused to determine one or more ROH score deficiencies of the user, based on the determined ROH score and the determined optimal ROH score for the user.

31. The system of claim 17, wherein determining the one or more neurotransmitter activity levels comprises, for each neurotransmitter of the plurality of neurotransmitters, summing the multiplied one or more values in the PE-NT matrix that correspond to the neurotransmitter.

32. The system of claim 31, wherein determining the one or more neurotransmitter activity levels comprises, for each neurotransmitter of the plurality of neurotransmitters, multiplying the summed value from the PE-NT matrix by a duration of the one or more activities of the user to determine the neurotransmitter activity level for the neurotransmitter.

33. A non-transitory computer readable storage medium storing one or more programs comprising instructions for assessing neurotransmitter levels of a user based on a user's activity data stored on a computing device, which, when executed by an electronic device with a display, cause the device to:
  receive data from a computing device associated with the user, wherein the received data is associated with one or more activities performed by the user;
  display a first graphical user interface at the display, wherein the first graphical user interface is configured to display and receive one or more categorizations of the one or more activities performed by the user from the user;
  determine one or more emotions based on the received one or more categorizations of the one or more activities performed by the user;
  display a second graphical user interface at the display, wherein the second graphical user interface is configured to receive one or more quantitative ratings corresponding to each of the determined one or more emotions from the user;
  determine one or more neurotransmitter activity levels of the user by applying the received one or more quantitative ratings received from the user to a positive emotion to neurotransmitter (PE-NT) matrix,
  wherein the PE-NT matrix indicates respective correspondences between a plurality of positive emotions and a plurality of neurotransmitters associated with one or more of the emotions of the plurality of positive emotions, such that, for each emotion of the determined one or more emotions from the user, the PE-NT matrix indicates one or more values, each value of the one or more values corresponding to a neurotransmitter of the plurality of neurotransmitters that is associated with the emotion, and
  wherein applying the received one or more quantitative ratings received from the user to the PE-NT matrix comprises multiplying one or more of the one or more values by a quantitative rating of the one or more quantitative ratings received from the user for the emotion;
  determine one or more optimal neurotransmitter activity levels for the user;
  determine one or more neurotransmitter deficiencies of the user, based on the determined one or more neurotransmitter activity levels of the user and the determined one or more optimal neurotransmitter activity levels for the user; and
  generate and display one or more suggestions for increasing the determined one or more neurotransmitter activity levels.

34. The non-transitory computer readable storage medium of claim 33, wherein the device is further caused to:
  display a third graphical user interface at the display, wherein the third graphical user interface is configured to display the determined one or more optimal neurotransmitter activities and the determined one or more neurotransmitter deficiencies.

35. The non-transitory computer readable storage medium of claim 34, wherein the further graphical user interface includes one or more user selectable features that when selected by the user allows the user to add an event corresponding to the one or more generated suggestions to an electronic calendar associated with the user.

36. The non-transitory computer readable storage medium of claim 33, wherein the generated one or more suggestions for increasing the determined one or more neurotransmitter are generated by selecting one or more entries from a database containing a plurality of suggestions for increasing neurotransmitter levels.

37. The non-transitory computer readable storage medium of claim 36, wherein the database containing a plurality of suggestions for increasing neurotransmitter levels is categorized based on one or more types of neurotransmitters.

38. The non-transitory computer readable storage medium of claim 36, wherein the database containing a plurality of suggestions for increasing neurotransmitter levels is categorized based on an amount of increase in the neurotransmitter levels needed.

39. The non-transitory computer readable storage medium of claim 33, wherein the categorizations received from the user comprises at least one category selected from the group consisting of: work and school, consumption, leisure, social, community service, religious, and spiritual.

40. The non-transitory computer readable storage medium of claim 33, wherein the determined one or more emotions comprises at least one emotion selected from the group consisting of: enthusiasm, sexual desire, pride, nuturant love, contentment, amusement, attachment love, pleasure, and gratitude.

41. The non-transitory computer readable storage medium of claim 33, wherein the second graphical user interface is configured to receive one or more lengths of time of the one or more activities performed by the user and determining the one or more neurotransmitter activity levels of the user includes applying the received one or more lengths of time of the one or more activities to the PE-NT matrix.

42. The non-transitory computer readable storage medium of claim 33, wherein the one or more neurotransmitter activity levels include one or more levels associated with: dopamine, testosterone, serotonin, oxytocin, cannabinoids, and opioids.

43. The non-transitory computer readable storage medium of claim 33, wherein determining the one or more emotions based on the received one or more categorizations of the one or more activities performed by the user is based on a behavior-to-positive emotion (B-PE) matrix.

44. The non-transitory computer readable storage medium of claim 33, wherein the device is further caused to determine an overall return on happiness (ROH) score based on the determined one or more neurotransmitter activity levels.

45. The non-transitory computer readable storage medium of claim 44, wherein the device is further caused to determine an optimal ROH score for the user.

46. The non-transitory computer readable storage medium of claim 45, wherein the device is further caused to determine one or more ROH score deficiencies of the user, based on the determined ROH score and the determined optimal ROH score for the user.

47. The non-transitory computer readable storage medium of claim 33, wherein determining the one or more neurotransmitter activity levels comprises, for each neurotransmitter of the plurality of neurotransmitters, summing the multiplied one or more values in the PE-NT matrix that correspond to the neurotransmitter.

48. The non-transitory computer readable storage medium of claim 47, wherein determining the one or more neurotransmitter activity levels comprises, for each neurotransmitter of the plurality of neurotransmitters, multiplying the summed value from the PE-NT matrix by a duration of the one or more activities of the user to determine the neurotransmitter activity level for the neurotransmitter.

* * * * *